United States Patent [19]
Bossi et al.

[11] Patent Number: 5,939,523
[45] Date of Patent: Aug. 17, 1999

[54] PURIFICATION OF DALBAHEPTIDE ANTIBIOTICS BY ISOELECTRIC FOCUSING

[75] Inventors: Alessandra Maria Bossi, Varese; Pier Giorgio Righetti, Milan; Ernesto Riva, Milan; Luigi Franco Zerilli, Milan, all of Italy

[73] Assignee: Gruppo Lepetit SpA, Milan, Italy

[21] Appl. No.: 08/981,368

[22] PCT Filed: Jun. 25, 1996

[86] PCT No.: PCT/EP96/02769

§ 371 Date: Dec. 18, 1997

§ 102(e) Date: Dec. 18, 1997

[87] PCT Pub. No.: WO97/02288

PCT Pub. Date: Jan. 23, 1997

[30]     Foreign Application Priority Data

Jul. 5, 1995 [EP] European Pat. Off. .............. 95110467
Jul. 24, 1995 [EP] European Pat. Off. .............. 95111583

[51] Int. Cl.⁶ .............................. A61K 38/14; C07K 9/00
[52] U.S. Cl. .................................. 530/317; 514/8; 514/9; 514/11
[58] Field of Search .................... 530/317, 333; 514/9, 8, 11

[56]                References Cited

U.S. PATENT DOCUMENTS

| | | | |
|---|---|---|---|
| 2,951,766 | 9/1960 | White | 106/18.31 |
| 4,322,343 | 3/1982 | Debono | 530/322 |
| 4,504,467 | 3/1985 | Molloy et al. | 424/118 |
| 4,521,335 | 6/1985 | Chan et al. | 530/322 |
| 4,552,701 | 11/1985 | Nagarajan et al. | 530/322 |
| 4,563,442 | 1/1986 | Clem et al. | 514/9 |
| 4,639,433 | 1/1987 | Hunt et al. | 514/8 |
| 4,643,987 | 2/1987 | Nagarajan et al. | 514/8 |
| 4,698,327 | 10/1987 | Nagarajan et al. | 514/8 |
| 4,742,045 | 5/1988 | Verma et al. | 514/8 |
| 4,782,042 | 11/1988 | Selva et al. | 514/9 |
| 4,804,534 | 2/1989 | Riva et al. | 424/118 |
| 4,868,171 | 9/1989 | Selva et al. | 514/183 |
| 4,882,313 | 11/1989 | Sitrin | 514/8 |
| 4,935,238 | 6/1990 | Selva et al. | 424/118 |
| 4,954,482 | 9/1990 | Maeda et al. | 514/8 |
| 4,954,483 | 9/1990 | Malabarba et al. | 514/8 |
| 4,971,670 | 11/1990 | Faupel et al. | 204/459 |
| 5,064,811 | 11/1991 | Borghi et al. | 514/8 |
| 5,185,320 | 2/1993 | Trani et al. | 514/8 |
| 5,194,424 | 3/1993 | Malabarba et al. | 514/8 |

FOREIGN PATENT DOCUMENTS

| | | |
|---|---|---|
| 0159180 | 10/1985 | European Pat. Off. . |
| 0201251 | 12/1986 | European Pat. Off. . |
| 0218099 | 4/1987 | European Pat. Off. . |
| 0231111 | 8/1987 | European Pat. Off. . |
| 0255256 | 2/1988 | European Pat. Off. . |
| 0259781 | 3/1988 | European Pat. Off. . |
| 0273727 | 7/1988 | European Pat. Off. . |
| 0276740 | 8/1988 | European Pat. Off. . |
| 0290922 | 11/1988 | European Pat. Off. . |
| 0326873 | 8/1989 | European Pat. Off. . |
| 0339982 | 11/1989 | European Pat. Off. . |
| 0351597 | 1/1990 | European Pat. Off. . |
| 0351684 | 1/1990 | European Pat. Off. . |
| 0351685 | 1/1990 | European Pat. Off. . |
| 0352538 | 1/1990 | European Pat. Off. . |
| 0356894 | 3/1990 | European Pat. Off. . |
| 0365319 | 4/1990 | European Pat. Off. . |
| 0370283 | 5/1990 | European Pat. Off. . |
| 0448940 | 10/1991 | European Pat. Off. . |
| 0525499 | 2/1993 | European Pat. Off. . |
| 0596929 | 5/1994 | European Pat. Off. . |
| 0560795 | 2/1996 | European Pat. Off. . |
| 0578644 | 12/1996 | European Pat. Off. . |
| 63017897 | 7/1986 | Japan . |
| 63-17897 | 1/1988 | Japan . |
| 8802755 | 4/1988 | WIPO . |
| 8902441 | 3/1989 | WIPO . |
| 8907612 | 8/1989 | WIPO . |
| 9011300 | 10/1990 | WIPO . |

OTHER PUBLICATIONS

Sitrin et al, Journal of Antibiotics, vol. 37, No. 11, pp. 1475–1478, Nov. 1984.

Bossi et al, Electrophoresis, vol. 17, (7), pp. 1234–1241, 1966.

Malabarba et al, J. Antibiotics, vol. 40, No. 11, (Nov. 1987) pp. 1572–1587.

Gauze, G.F., et al, Eremomycin, a novel cyclic glycopeptide antibiotic. Antibiot. Med. Biotecknol. 1987; 32: 571–576 (English Translation).

Berdnikova, T.F. et al, Structure of the aglycone of eremomycin, a novel antibiotic of the group of polycyclic glycopeptides. Antibiot. Kimioter. 1988; 33: 566–570 (English Translation).

Lomakina, N.N., et al, Structure of eremosamine, an amigo sugar from eremomycin. Antibiot. Kimioter. 1988; 33: 726–729 (English Translation).

Parenti et al, Drugs of the future, vol. 15(1), pp. 57–72, (1990).

Cavalleri et al, "Glycopeptides (dalbaheptides)", Kirk–Othmer's Encyclopedia of Chemical Technology, vol. 2, pp. 995–1018, J. Wiley & Sons, 1992.

Sztaricskai et al, The Chemistry of the Vancomycin Group of Antibiotics. In: Recent Developments in the Chemistry of Natural Carbon Compounds, vol. X. R. Bogner and Cs. Szantay (Eds.). Akademiai Kaido 1984; pp. 91–201.

(List continued on next page.)

*Primary Examiner*—Cecilia J. Tsang
*Attorney, Agent, or Firm*—Ruth E. Homan

[57]                ABSTRACT

Method for purifying antibiotic compounds of the dalbaheptide family by means of isoelectric focusing (IEF) in a multicompartinent electrolyzer with immobiline membranes, in particular zwitterionic membranes. A further object of the invention are pure antibiotic compounds obtainable according to the present process, in particular the pure $6^B$-decarboxy-$6^B$-(hydroxymethyl)-$N^{63}$-3-(dimethylamino) propyl amide derivatives of antibiotic A40926.

13 Claims, 7 Drawing Sheets

OTHER PUBLICATIONS

Righetti et al, J. Chromatogr. 475, pp. 293–309 (1989).

Williams, D.H., et al, Structure of the antibiotic ristocetin A.J.C.S. Chem. Comm. 1979: 906–908.

Debono, M. et al, Actaplanin, new glycopeptide antibiotics produced by Actinoplanes missouriensis. The isolation and preliminary chemical characterization of actaplanin, J. Antiboit. 1984; 37: 85–95.

Hunt, A.H.. et al, Structures of the actaplanins. J. Org. Chem. 1984; 49: 641–645.

Borghi, A., et al, Teichomycins, new antibiotics from Actinoplanes teichomycetius nov.sp.IV. Separation and characterization of the components of teichomycin (teicoplanin). J. Antibiot. 1984; 37: 615–626.

Coronelli, C., et al, Teicoplanin: chemical physico–chemical and biological aspects. Farm Ed. Sci. 1987; 42: 767–786.

Barna, J.C.J, et al, Structure elucidation of the teicoplanin antibiotics. J. Am. Chem. Soc. 1984; 106: 4895–4902.

Michel, K.H., et al, A35512, a complex of new antibacterial antibiotics produced by Streptomyces cadnidus. I. Isolation and Characterization. J. Antibiot. 1989; 33: 1397–1406.

Harris, C.M., et al Structural studies of glycopeptide antibiotic A35512B. Identification of the diphenyl ether–type bis (amino acid). Tetrahedron 1983; 39: 1661–1666.

Eggert, J.H., et al, A41030, a complex of novel glycopeptide antibiotics. Discovery, fermentaiton, isolation and characterization. 23rd Intersci. Conf. Antimicrob. Agents Chemother (Oct 24–26, Las Vegas) 1983; Abst. 440.

Hunt, A.H. et al, Structure of Antibiotic A41030A, J. Org. Chem. 1985; 50: 2031–2035.

Boeck, L.D., et al, A47934, a novel glycopeptide–aglycone antibiotic produced by a strain of Streptomyces toyocaensis. Taxonomy and fermentation studies. J. Antibiot. 1986; 39: 1533–1540.

Hunt, A.H., et al, A47934 and A41030 factors–new glycopeptides and glycopeptide aglycones: structure determination. 32rd Intersci. Conf. Antimicrob. Agents Chemother. (Oct. 24–26, Las Vegas) 1983; Abst. 441.

Sitrin, R.D, et al, Aridicins, novel glycopeptide antibiotics. II. Isolation and characterization. J. Antibiot. 1985; 38:561–571.

Jeffs, P.W. et al, Structure of aridicin A. An integrated approach employing 2D NMR, energy minimization, and distance constraints. J. Am. Chem. Soc. 1986; 108: 3063–3075.

Roberts, G.D., et al, Structural characterization of glycopeptide antibiotics related to vancomycin by Bast Atom Bombardment Mass Spectrometry. J. Antibiot. 1985; 38: 713–720.

Riva, E., et al, Column purification and HPLC determination of teicoplanin and A40926. Chromatographia 1987; 24: 295–301.

Waltho, J.P., et al, Structure elucidation of the glycopeptide antibiotic complex A40926. J. Chem. Soc., Perkin Trans. I, 1987, 2103–2107.

Folena–Wasserman, G., et al, Kibdelins (AAD–609), novel glycopeptide antibiotics. II. Isolation, purification, and structure. J. Antibiot. 1986; 39: 1395–1406.

Christensen, S.B., et al, Parvodicin, a novel glycopeptide from a new species, Actinomadura parvosata; discovery, taxonomy, activity and structure elucidation, J. antibiot. 1987; 40: 970–990.

Huber, F.M., et al, Preparation and characterization of some bromine analogs of the glycopeptide antibiotic actaplanin. J. Antibiot. 1988; 41: 798–801.

Cometti, A., et al, Isolation and structure determination of the main related substancs of teicoplanin, a glycopeptide antibiotic. II Farmaco, Ed. Sci., 1988; 43: 1005–1018.

Borghi, A., et al, Isolation and structure determination of two new analogs of teicoplanin, a glycopeptide antibiotic. J. antibiotic 1989; 42: 361–366.

Malabarba, A., et al, Teicoplanin, antibiotics from Actinoplanes teichomyceticus nov. sp. VII Preparation and NMR characteristic of the aglycone of teicoplanin. J. Antibiot. 1986; 39: 1430–1442.

Malabarba, A. et al, Teicoplanin, antibiotics from Actinoplanes teichomyceticus nov. sp. VI. Chemical Degration: physico–chemical and biological properties of acid hydrolysis products. J. Antibiot. 1984, 37: 988–999.

Kamogashira, T. et al, A new glycopeptide antibiotic, OA–7653, produced by Streptomyces hygroscopicus subsp. hiwasaensis. Agric. Biol. Chem. 1983; 47: 499–506.

Jeffs, P.W., et al, Structure of the antibiotic)A–7653, J. Org. Chem. 1988; 53: 471–477.

Boeck, L.D., et al, N–Demethylvancomycin, a novel antibiotic produced by a strain of Nocardia orientalis. Taxonomy and fermentation. J. Antibiot. 1984; 37: 446–453.

Hunt, A.H., et al, A51568A: N–demethylvancomycin. J. Antibiot. 1984; 37: 917–919.

Tsuji, N. et al, New glycopeptide antibiotics. I. The structures of orienticins. J. Antibiot. 1988; 41: 819–822.

Gauze, G.F., et al, Eremomycin, a novel cyclic glycopeptide antibiotic. Antibiot. Med. Biotecknol. 1987; 32: 571–576 (Need English Equiv).

Brazhnikova, M.G., Properties of eremomycin, a new glycopeptide antibiotic. 2nd Int. Symp. on "New Bioactive Metabolites from Microorganisms" (May 2–7)Gera) 1988; Post 40.

Berdnikova, T.F. et al, Structure of the aglycone of eremomycin, a novel antibiotic of the group of polycyclic glycopeptides. Antibiot. Kimioter. 1988; 33: 566–570.

Lomakina, N.N., et al, Structure of eremosamine, an amino sugar from eremomycin. Antibiot. Kimioter. 1988; 33: 726–729 (Need English Equiv).

Riva, E. et al, A42867, a novel glycopeptide antibiotic. J. Antibiot. 1989; 42: 497–505.

Hamill, R.L., et al, A82846, a new glycopeptide complex, produced by Amycolatopsis orientalis. 2. Isolation and characterization. 28th Intersci. Conf. Antimicrob. Agents Chemother. (Oct 23–26, Los Angeles) 1988; Abst. 975.

Hunt, A.H., et al, A82846, a new glycopeptide complex, produced by Amycolatopsis orientalis. 3. Structure determination. 28th Intersci. Conf. Antimicrob. Agents Chemother. (Oct 23–26, Los Angeles) 1988; Abst. 976.

Tsuij, N. et al, New glyco peptide antibiotics: II. The isolation and structures of chloro orienticins. J. Antibiot. 1988; 41: 1506–1510.

Harris C.M., et al, The role of the chlorine substituents in the antibiotic vancomycin: preparation and characterization of mono– and didechlorovancomycin. J. Am. Chem. Soc. 1985; 107: 6652–6658.

Batta, G. et al, 13C NMR study of antinoidins: carbohydrate moieties and their glycosidic linkages. J. Antibiot. 1986; 39: 910–913.

Heald, S.L. et al, Actinoidins A and A2: structure determination using 2D NMR methods. J. Antibiot. 1987; 40: 630–645.

Okazaki, T. et al, A chloropolysporins A,B and C, novel glycopeptide antibiotics from *Faenia interjecta* sp. nov. I. Taxonomy of producing organism. J. Antibiot. 1987; 40: 917–923.

Takatsu, T. et al, Chloropolysporins A,B and C, novel glycopeptide antibiotics from *Faenia interjecta* sp. nov. II Fermentaiton, isloation and physico–chemical characterization, J. Antibiot. 1987; 40: 924–932.

Takatsu, T., et al, Chloropolysporins A,B and C, novel glycopeptide antibiotics from *Faenia interjecta* sp. nov. III. Structure elucidation of chloropolysporins. J. Antibiot. 1987; 40:933–940.

Dingerdissen, J.J. et al,Actinoidin A2 a novel glyco peptide: production, preparative HPLC separation and characterization. J. Antibiot. 1987; 40: 165–172.

McGahren, W.J. et al, Components and degradation compounds of the avoparcin conplex. J. Antibiot. 1983; 36: 1671–1682.

Arjuna Rao, V., et al, Synmonicins: a novel antibiotic complex produced by *Synnemomyces mamnoorii* gen. et sp. nov. I. Taxonomy of the producing organism, fermentation and biological properties, 26th Intersci. Conf. Antimicrob. Agents Chemother. (Sep. 28–Oct. 1, New Orleans) 1986; Abst. 939.

Verma, A.K., et al, Synmonicins: a novel antibiotic complex. II. Isolation and preliminary characterization. 26th Intersci. Conf. Antimicrob. Agents Chemother. (Sep. 28–Oct. 1), Las Vegas) 1986; Abst. 940.

Righetti, P.G., et al, (199) J. Chromatogr. 500, 681–696.

Ettori, C., et al, (1992) J. Biotechnol. 25, 307–318.

Wenisch E., et al, (1992) Electrophoresis 13, 668–673.

Weber, W. et al, (1994) J. Chromatogr. A 679, 181–189.

Wenisch, E., et al, (1994) Electrophoresis 15, 647–653.

Breton, J., et al, (1995) J. Chromatogr. A, in press.

Wenisch E., et al, (1993) J. Biochem. Biophys. Methods 27, 199–213.

Righetti, P.G., (1990) Immobilized pH Gradients; Theory and Metodology, pp. 64–68, Elsevier, Amsterdam.

Righetti, P.G. et al, (1978) J. Chromatogr. 157, 243–251.

Henner, J. et al, (1984) J. Antib., 11, 1475–1478.

Sahai, et al, Antimicrob. Agents Chemother. (1990), 34(5), 765–769.

Rilbe, H., (1973) Ann. N.Y. Acad. Sci., 209, 11–22.

PURIFICATION OF DALBAHEPTIDE ANTIBIOTICS BY ISOELECTRIC FOCUSING

This application is a 371 of PCT/EP96/02769.

The present invention refers to a method for purifying antibiotic compounds of the dalbaheptide family by means of an electrophoretic technique known as isoelectric focusing.

More precisely, the present purification method refers to isoelectric focusing (IEF) of dalbaheptide antibiotics in a multicompartment electrolyzer with IMMOBILINE membranes, in particular zwitterionic membranes.

A further object of the invention are pure antibiotic compounds obtainable according to the present process, in particular the pure $6^{B\text{-}decarboxy}\text{-}6^{B\text{-}(hydroxymethyl)\text{-}N63}$-3-(dimethylamino)propyl amide derivative of antibiotic A40926.

A thorough description of the principles and methods of IEF in multicompartment electrolyzer with IMMOBILINE membranes can be found in ref. 5.

According to this technique, the compound to be purified is an amphoteric substance characterized by having a determined isoelectric point (pI), and good buffering properties at the pI value (see ref. 102). The mixture to be purified is contained in a liquid vein and it is trapped into one of a set of chambers, said chamber being delimited by two IMMOBILINE membranes having isoelectric points encompassing the pI of the desired compound. Thus, by a continuing electrophoretic titration process, all other impurities, either non-isoelectric or with different pI values are forced to leave the chamber, towards more anodic or cathodic chambers, while the purified compound is left into the initial chamber.

This purification technique has been applied to a number of proteins such as eglin C (ref. 5), monoclonal antibodies against the gp-41 of the AIDS virus (ref. 103), recombinant human growth hormone (ref. 104), the epidermial growth factor receptor (refs. 105 and 106), recombinant superoxide dismutase (ref. 107), interleukin (ref. 108) and glucoamylase (ref. 109).

The present invention discloses for the first time a suitable methodology for applying such IEF purification technique to rather small molecules, with a molecular weight of about 1800 daltons, and specifically to the antibiotic compounds of the dalbaheptides family.

With the term dalbaheptides are usually defined all antibiotic substances having in common a highly modified linear heptapeptidic structure made up of seven amino acids, five of which are constantly aryl- and arylmethyl-amino acids, said structure being determinant of a common mechanism of action, i.e. the specific complexation with the D-alanyl-D-alanine terminus of one or more intermediates of the cell wall synthesis which leads to cell disruption. The term dalbaheptide thus derives from the wording D-al{anyl-D-alanine} b{inding} a{ntibiotics} {having} hept{apept}ide {structure}.

The dalbaheptide antibiotics can conventionally be represented by the following general formula I

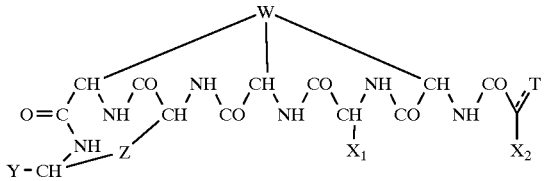

wherein:
W, Z, $X_1$, $X_2$ and T represent the relative portions of an antibiotic of the dalbaheptide group; and Y represents a carboxyacid group or a functional derivative thereof.

The formula I includes the salts of dalbaheptide antibiotics with acids and bases as well as their inner salts.

In the general structure represented by the formula I, the above mentioned five fundamental aryl- and arylmethylaminoacids are those connected with the moieties Z and W. Apart from slight differences in the substitutions on the respective aryl portion, the five aryl- and arylmethyl aminoacids are substantially common to all members of the dalbaheptide antibiotics group, while the different type and structure of the two remaining aminoacid portions which bear the substituents $X_1$ and $X_2$ allow a further classification of the dalbaheptides so far known into four different sub-groups, each of which is referred, for practical reasons, to a well known antibiotic of the group that, in the previous scientific literature, has been generally identified as glycopeptide antibiotics.

Said four sub-groups can be defined respectively as ristocetin-type, vancomycin-type, avoparcin-type and synmonicin-type antibiotics.

For a detailed classification of the dalbaheptide antibiotics see references 1 and 2.

According to the terms and definitions of this specification, the dalbaheptide antibiotics as well as the four sub-groups into which they are presently classified, include both products produced as metabolites of microbial strains, as well as semisynthetic derivatives thereof.

The fermentation products generally bear sugar moieties conjugated with the hydroxy groups positioned on the aryl or arylmethyl portions of the five fundamental aminoacids, or on the $X_1$ and/or $X_2$ moieties when they contain hydroxylated aromatic ring moieties. In a few cases, one phenolic hydroxy function may be esterified with a sulfuric acid moiety. In the fermentation products the function represented by the symbol Y generally is a carboxyacid or a lower alkyl carboxyester, while the symbol T, in general, represents an amino or a lower alkyl amino (e.g. methylamino) moiety.

The semisynthetic derivatives described in the patents and scientific literature are, for instance, products deriving from complete or partial hydrolysis of the sugar portions, thus having free hydroxy groups on the aryl or the arylmethyl portions, products deriving from the elimination of the benzylic hydroxy group on the arylmethyl portions, products deriving from the introduction of specific sugar moieties or aliphatic or alicyclic moieties on a phenolic hydroxy function, products deriving from the modifications of the carboxylic moiety Y to form functional derivatives thereof, e.g. esters, amide or hydrazide derivatives or products deriving from the modification of the portion T yielding variously substituted amino groups (e.g. by alkylation or acylation) or resulting from the introduction of protecting groups of said aminic function or products deriving from the acylation of the aminic moieties of the amino sugar moieties, or products resulting from the dehalogenation of the aryl moieties originally containing halo substituents or products deriving from the introduction of halo (preferably chloro, bromo and iodo) substituents on the aryl moieties. Said semisynthetic derivatives may contain more than one of the above mentioned modifications of the basic structure of the natural products.

According to a more specific representation, most of the dalbaheptide antibiotics, the structure of which has been so far determined, can be represented by the formula I wherein the symbol W represents the partial structure:

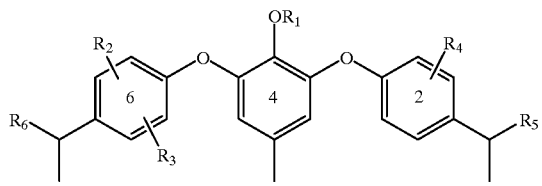

wherein $R_1$ is hydrogen, a sugar moiety, an aliphatic or alicyclic hydrocarbon moiety. $R_2$, $R_3$ and $R_4$ are each independently, hydrogen or halogen, preferably chloro or bromo, and are most preferably in the ortho position with respect to the ether bond. $R_5$ and $R_6$ are each independently hydrogen, or a group $OR_7$ wherein $R_7$ is hydrogen or a sugar moiety. As shown in formula I above, the group W is simultaneously linked to the second, fourth and sixth aminoacid moiety (starting from the right) of the heptapeptidic chain of dalbaheptides; and the symbol Z represents the partial structure:

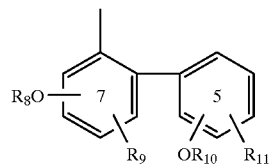

wherein the groups $OR_8$ and $OR_9$, preferably, are respectively in the para and ortho position with respect to the bond connecting the two phenyl rings and the radical $R_8$ and $R_9$ each independently represents hydrogen or a sugar moiety; most preferably $R_8$ is hydrogen. The group $OR_{10}$ is, preferably, in the position ortho with respect to the bond connecting the two phenyl rings and the radical $R_{10}$ represent hydrogen or a sugar moiety. The group $R_{11}$ is, preferably, in the position meta with respect to the bond connecting the two phenyl rings and represent hydrogen or halogen, most preferably, hydrogen or chloro. As shown in formula I, the group Z is linked to the fifth and seventh aminoacid moiety (starting from the right) of the heptapeptidic chain of dalbaheptides.

The meanings of the symbols $X_1$ and $X_2$ which permit the differentiation of the so far known dalbaheptide antibiotics into four sub-groups are respectively the following:

$X_1$ represents a phenyl or a benzyl group wherein the phenyl ring may optionally bear one or two substituents selected from halogen, preferably chloro, lower alkyl, preferably methyl, and hydroxy wherein the hydroxy group can be optionally conjugated with a sugar moiety through an acetalic bond or esterified with a sulfuric acid residue, or it may also represent a $(C_1-C_2)$ aliphatic moiety substituted with a carboxylic or carboxamide function, a thiomethyl or a methylsulfinyl group;

$X_2$ represents a phenyl group which may optionally bear one or two substituents selected from halogen, preferably chloro, lower alkyl, preferably methyl, and hydroxy wherein the hydroxy group can be optionally conjugated with a sugar moiety through an acetalic bond, or it may represent a $(C_1-C_4)$ aliphatic moiety, preferably methyl or isobutyl;

or $X_1$ and $X_2$ taken together represent a oxybis (phenylene) moiety where one or both phenyl rings may optionally be substituted as indicated above.

According to a more specific representation of most of the dalbaheptide antibiotics of formula I so far known (including the semisynthetic derivatives thereof), the symbol T, preferably identifies an aminic group wherein one or both hydrogen atoms may optionally be substituted by an alkyl radical of 1 to 12 carbon atoms which, in turn, can optionally bear one or more substituents, by a $(C_4-C_7)$ cycloalkyl, by an acyl radical or by a suitable protecting group of the aminic function or T may also represent a tri(lower alkyl) ammonio radical, the positive charge of which is neutralized by an anion deriving from either a strong acid or an internal acid function, e.g. a carboxylate anion deriving from the carboxyacid moiety represented by the symbol Y. In some cases T may also represent hydrogen (e.g. teicoplanin semisynthetic derivatives) or a hydroxy, oxo or oxymino moiety (e.g. ristocetin derivatives). Accordingly, when T is a divalent radical the dotted line in formula I represents an additional bond.

The symbol Y represents a carboxy group, a functional derivative thereof such as a carboxyester, a carboxamide, a carbohydrazide group or a hydroxymethyl moiety. This definition includes the naturally occurring lower alkyl esters as well as the esters formed by reaction of the carboxylic function with alcohols, e.g. aliphatic alcohols bearing substituents in the aliphatic chain, and includes also a wide series of substituted amides which are formed by reaction of the carboxy group with aliphatic, cycloaliphatic and heterocyclic amines. In particular the aliphatic amine may contain substituents on the aliphatic chain such as amino, lower alkylamino, di-lower alkylamino, hydroxy, lower alkoxy, carboxy, carbamyl, substituted carbamyl and the like.

The salts of the end compounds of formula I can be those deriving from the salification with an acid of the basic functions of the molecule, e.g. the aminic function identified by the symbol T, or an aminic function contained as substituent in the carboxyester, carboxamide or carbohydrazide moiety represented by the symbol Y or in a sugar moiety (e.g. vancomycin, avoparcin). Alternatively, the salts may be formed through salification of the carboxylic acid function represented by the symbol Y, or an acidic function contained as substituent in the carboxyester or carboxamide moiety or any acidic function which may be present in any other portion of the molecule, with an appropriate base. The inner salts are those formed through internal salification in the cases of simultaneous presence of basic (e.g. aminic) and acid (e.g. carboxylic) functions of sufficient strength in the dalbaheptide precursor and/or the pentapeptide end compounds.

In the dalbaheptide antibiotics, the sugar moieties which can be linked to the hydroxy groups are either mono-or polysaccharides which can be acetylated or methylated in one of the hydroxylic groups or deoxygenated in one or two positions and may bear carboxylic or aminic substituents which can be acylated, for instance, by aliphatic acid radicals. Specific sugar moieties can be introduced through chemical or microbiological reactions on dalbaheptide substrates having free hydroxy groups on the aromatic rings.

Typical examples of unsubstituted monosaccharide moieties linked to the hydroxy groups of the basic dalbaheptide structure include both hexoses and pentoses such as, for instance: glucose (e.g. actaplanin $B_2$), galactose (e.g. antibiotic A 41030C), mannose (e.g. teicoplanin $A_2$), fucose (e.g. antibiotic A 35512 B), rhamnose (e.g. avoparcin) and acetyl mannose (e.g. parvodicin $C_3$).

Typical examples of carboxy or amino substituted monosaccharide moieties linked to the hydroxy groups include N-acetyl glucosamine (e.g. teicoplanin $A_2$ complex), N-($C_9$–$C_{12}$) aliphatic acyl glucosamine (e.g. teicoplanin $A_2$ complex), ristosamine (e.g. ristocetin A), actinosamine (e.g. actinoidin A), N-($C_9$–$C_{12}$)aliphatic acyl-2-amino-2-deoxyglucuronic acid (e.g. ardacins).

Typical examples of polysaccharide moieties may contain both unsubstituted and carboxy or amino substituted sugars units such as glucose (e.g. actaplanin A), mannose (e.g. ristocetin A) (e.g. ristocetin A), rhamnose (e.g. ristocetin B), olivose (e.g. orienticin B), vancosamine (e.g. vancomycin) epi-vancosamine (e.g. orienticin A, C and D), acosamine, (e.g. actinoidin), and ristosamine (e.g. avoparcin), linked with at least another sugar unit. In the dalbaheptides so far known and whose structure have been determined, polysaccharides containing up to four sugar units have been identified.

The characteristics which allow a further classification of the so far known dalbaheptides into four sub-groups are in no way limiting the scope of this invention in that new natural products and derivatives thereof falling into the general classification of dalbaheptide antibiotics can be obtained and identified which can be purified according to the IEF process of this invention. However, for a more precise identification of representative compounds which can be purified according to the process of the present invention, in the following is given a further detailed description of the four sub-groups mentioned above and of the corresponding representative compounds.

Referring to the formula I above, the sub-group identified as ristocetin-type dalbaheptides is characterized in that the symbols $X_1$ and $X_2$ taken together represent an oxybis (phenylene) moiety wherein one or both phenyl rings may optionally bear one or two substituent selected from halogen, preferably chloro, lower alkyl, preferably methyl, and hydroxy wherein the hydroxy group can be optionally conjugated with a sugar moiety through an acetalic bond or esterified with a sulfuric acid residue.

Dalbaheptide antibiotics which can be assigned to this sub-group include the following:

ristocetin (ref. 6), actaplanin (ref. 7, 8), teicoplanin (ref. 9, 10, 11), antibiotic A35512 (ref. 12, 13), antibiotic A41030 (ref. 14, 15), antibiotic A47934 (ref. 16, 17), ardacin A, B, C (ref. 18, 19, 20), antibiotic A40926 (ref. 21, 22, 23), kibdelin (ref. 24), parvodicin (ref. 25), and antibiotic UK 68597 (ref. 26).

The semisynthetic derivatives of the above mentioned natural products are also included in this sub-group. See, for instance, the aglycone and pseudoaglycones of ardacins (ref. 27) and the derivatives thereof wherein Y is a carboxamide or a carbohydrazide moiety (ref. 28); the aglycone and pseudoaglycone of parvodicin (ref. 29); the hydrolysis products of actaplanins (ref. 30); the conversion products of the first aminoacid moiety of ristocetin A, antibiotic A 35512, A 41030 and A 47934 to the corresponding keto-analogs (ref. 31 and 32); the acylation derivatives of ristocetin, actaplanin and their pseudoaglycons (ref. 33), the bromine analogs of actaplanin (ref. 34); the aromatic aldehyde derivatives of ristocetin (ref. 35); the derivatives of teicoplanin and antibiotic A40926, to which specific mention is made in the following.

The dalbaheptide antibiotic sub-group identified as vancomycin-type dalbaheptides is characterized by the fact that in formula I the symbol $X_1$ represents a ($C_1$–$C_2$) aliphatic rest substituted with a carboxylic or carboxamide function and the symbol $X_2$ represents a ($C_1$–$C_4$)aliphatic rest. In particular, in the most common examples of antibiotic substances falling within this sub-group, $X_1$ is a residue deriving from aspartic acid, aspargine or glutamine, while $X_2$ is a residue deriving from alanine or leucine.

Some vancomycin-type dalbaheptides (e.g. M43A, B and C, ref. 55) are further characterized by the fact that T represents a trimethylammonio group whose positive charge is neutralized by the carboxylate anion formed by the carboxylic group represented by the symbol Y.

Other dalbaheptide antibiotics which can be assigned to this sub-group include the following:

OA-7653 (ref. 51, 52), A 51568 A and B (ref. 53, 54), orienticins (ref. 56, 57), eremomycin (ref. 58, 59, 60, 61), A 42867 (ref. 50, 62), A 82846 (ref. 63, 64), chloroorienticins (ref. 65), MM 47761 and MM 49721 (ref. 94), decaplanin (ref. 95), MM 45289 and MM 47756 (ref. 96).

The semisynthetic derivatives of the above mentioned natural products are included in this sub-group. See for instance: the variously glycosylated derivatives of the hydrolysis products of vancomycin, A 51568A and B and M 43D (ref. 66); the desvancosaminyl and des(vancosaminyl-O-glucosyl)-derivatives of vancomycin, A 51568A; A 51568B, M 43A and M 43B (ref. 67), the derivatives of A 82846 (ref. 93); the reaction products of the aminic rests of some vancomycin-type dalbaheptides with aldehydes and ketones and the corresponding hydrogenation products (ref. 68, 69), the N-acyl derivatives of vancomycin-type antibiotics (ref. 70, 71), mono- and didechlorovancomycin (ref. 72) and the hydrolysis products of eremomycin (ref. 60).

The avoparcin-type dalbaheptide sub-group is characterized by the fact that the symbol $X_1$ in formula I represents a phenyl or benzyl group wherein the phenyl ring may optionally bear one or two substituents selected from hydroxy and halogen, preferably chloro, the symbol $X_2$ represents a phenyl group which may optionally bear one or two substituents selected from halogen, preferably chloro, and hydroxy which may optionally be conjugated with a sugar moiety (e.g. rhamnose).

Other dalbaheptide antibiotics which can be assigned to this group include the following:

actinoidin A, B (ref. 3, 75, 76), chloropolysporin A, B, C (ref. 77, 78, 79), actinoidin $A_2$ (ref. 80, 76) and helvecardin A, B (ref. 26), MM 47767, MM 55256 (ref. 92).

Semisynthetic derivatives of avoparcin-type sub-group of dalbaheptide antibiotics are for instance the demannosyl chloropolysporin B derivatives, the chloropolysporin pseudoaglycone, the derhamnosyl alpha and beta avoparcin (ref. 81), the mannosyl aglycones of avoparcin (LL-AV290) and other derivatives wherein one or more sugar moieties are hydrolyzed (ref. 84).

The dalbaheptide antibiotics sub-group identified as synmonicin-type antibiotics is characterized by the fact that in formula I the symbol $X_1$ represents a $C_2$ alkyl rest substituted on the terminal carbon with a thiomethyl or methylsulfinyl group, and the symbol $X_2$ represent a phenyl group bearing a hydroxy substituent which may be conjugated with a sugar moiety. Synmonicin (CWI-785) complex, its components and some of its hydrolysis products (ref. 86, 87, 88) seem to be, for the moment, the only members of this sub-group.

As said above, a particular compound which can be assigned to the ristocetin-type dalbaheptides is the teicoplanin $A_2$ complex, of general formula In the semisynthetic derivatives, the aminic rest on the $C^{15}$ identifies an aminic radical modified by reaction with protecting groups or by conversion into the corresponding alkylamino or dialkylamino group wherein the alkyl portion (s) can bear further substituents according to ref. 85, 89, 90 and 91. Teicoplanin derivatives presenting modifications in

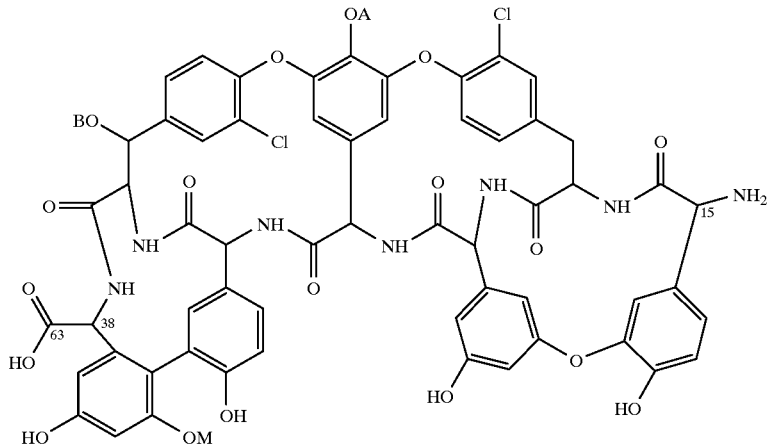

wherein A, B and M represent the sugar moieties linked to the molecule core in the natural products.

Within the term "teicoplanin" are comprised the single components of the fermentation complex (ref. 9) and related substances (ref. 36, 37) as well as the aglycone, pseudoaglycones (ref. 4, 38, 39, 40) and the semisynthetic derivatives thereof.

The chemical structures of the semisynthetic derivatives of teicoplanin which are particularly interesting for their biological activity have the same basic structure of the teicoplanin main components, the related substances, aglycone and pseudoaglycone with the modifications of either/both the $C^{63}$ carboxy group or/and the aminic rest on the $C^{15}$. In particular, the $C^{63}$ carboxy rest corresponding to the symbol Y in the formula I above has been modified to the corresponding esters according to ref. 41 and carboxamide group $CONR_{14}R_{15}$ according to the meanings set forth respectively in ref. 73, 74, 82 and 83.

both $C^{63}$ carboxylic group and aminic rest on the $C^{15}$ and processes for their manufacture have been described in ref. 83 and 98.

Other semisynthetic teicoplanin derivatives described in the prior art include the esters and hydrazides of the $C^{63}$ carboxy group (ref. 41 and 42), the de-acetyl glucosaminyl-deoxy teicoplanins (ref. 43) and the corresponding $C^{63}$ carboxyamides (ref. 44), the mono and di-dechloroderivatives of teicoplanin (ref. 45), the $O^{56}$ alkyl and cycloalkyl derivatives of teicoplanin aglycone and pseudoaglycones (ref. 46 and 97) and the 38-decarboxy-38-hydroxymethyl derivatives (ref. 99).

A further compound falling within the ristocetin-type dalbaheptides sub-group is antibiotic A 40926 complex and its main factors (refs. 21, 22, 23), defined by the following general formula

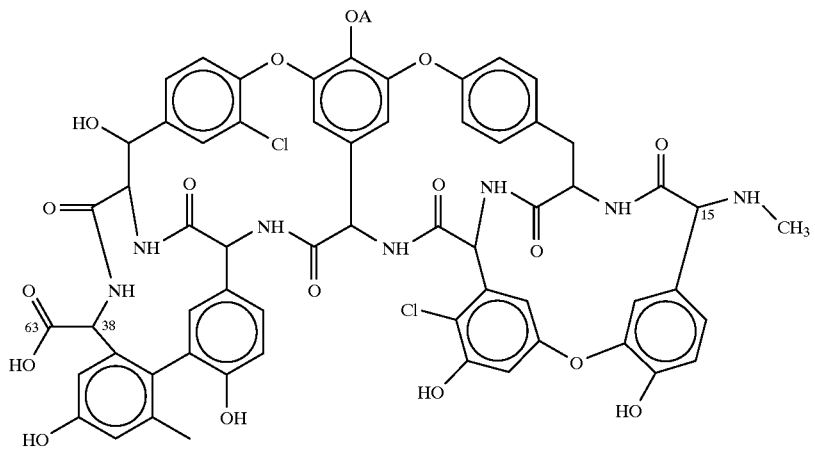

wherein A and M represent the sugar moieties linked to the molecule core in the natural products.

As well as for teicoplanin, a number of derivatives of antibiotic A 40926 have been disclosed; among those are the aglycon thereof (ref. 48), the mannosyl aglycon (ref. 47), the N-acylamino-deoxy-glycuronyl aglycones (ref. 48), the deacyl derivatives (ref. 49), the $C^{63}$-ester derivatives (ref. 100) and the $C^{63}$-amide derivatives (ref. 101).

Ref. 101 discloses, among others, the preparation of the $6^B$-decarboxy-$6^B$-(hydroxymethyl)-$N^{63}$-3-(dimethylamino) propyl amide derivative of antibiotic A40926. This compound is prepared by reacting the $6^B$-decarboxy-$6^B$-(hydroxymethyl) antibiotic A40926 with dimethylpropylamine in the presence of the condensing agent benzotriazolyloxy-tris-(pyrrolidino)phosphonium hexafluorophosphate (PyBOP). The so obtained product contains however some undesired impurities which can not be removed under conventional chromatographic procedures.

As said above, one object of the present invention is to provide a purification method based on isoelectric focusing for purifying the above dalbaheptide antibiotics from undesired impurities.

Said impurities to be separated, may be either minor components of an antibiotic complex mixture obtained from a fermentation process or side-products of chemical reactions to which the antibiotic compound has been submitted for obtaining semisynthetic derivatives thereof.

For instance, it is known that a dalbaheptide antibiotic complex (either natural or semisynthetic) may contain some impurities which elicit histamine release when administered to patients; depending on the specific dalbaheptide antibiotic, said histamine release may be more or less marked (see ref. 114). Such histamine release has also been observed, for instance, in the case of the $6^B$-decarboxy-$6^B$-(hydroxymethyl)-$N^{63}$-3-(dimethylamino)propyl amide derivative of antibiotic A40926 complex.

As these impurities are, in general, hardly detectable, and thus hardly individually removable, a method which allows the separation of all the impurities from the active substances is highly desirable.

The present IEF purification is thus a powerful tool for eliminating impurities which could not be eliminated by an array of conventional chromatographic procedures, including RP-HPLC. It is furthermore a method which can be applied for the purification of the dalbaheptide antibiotics on industrial scale.

The main obstacle in applying the IEF technique for the purification of dalbaheptide antibiotics, in common with all focusing methodologies, is that, at its pI value, the compound to be purified shows a very limited solubility. The preparation of a suitable supporting solution of the analyte at its pI value, able to maintain the solubility of the compound to be purified also at relatively high concentrations, is thus one of the main problems to solve; in fact, upon precipitation, also the impurities would co-precipitate with the main fraction.

It has now been found that an aqueous solution of urea and a zwitterionic detergent is suitable for solubilizing the dalbaheptide antibiotic compounds; particularly suitable have been found mixtures of urea with detergents of the CHAPS family, i.e. the sulfobetaine zwitterionic derivatives of cholic acid, e.g. {3-[3-(cholamidopropyl)-dimethylammonio]}-1-propanesulfonate or {3-[3-(cholamidopropyl)-dimethylammonio]}-2-hydroxy-1-propanesulfonate; among those, preferred is {3-[3-(cholamidopropyl)-dimethylammonio]}-1-propanesulfonate.

The urea/CHAPS ratio in the mixtures and the concentration thereof will depend on the specific dalbaheptide compound to purify. In general, it has been found that the concentration of urea in the solution can vary in the range from about 4M to 8M; for instance, when mixtures containing 63-amide derivatives of antibiotic A40926 are involved in the IEF purification of the invention, a preferred concentration of urea is about 8M. A suitable concentration of CHAPS detergents in the IEF supporting solution may be from about 1% to 5% (w/v); preferably, the concentration is from 2% to 4.5%. Particularly preferred for purifying mixtures obtained from amidation of antibiotic A40926 is a concentration of about 3.5%.

The pI values of each dalbaheptide antibiotic substance may be easily determined according to common analytical procedures, such as by electrophoresis on analytical immobilized pH gradient gels (IPG gels). A suitable methodology for the determination of the pI values using IPG gels is described in ref. 112.

Theoretical calculation of the pI values, based on the pK values of the acid and/or basic groups of the antibiotic molecule, may lead to uncorrect results, because of possible interactions of the acid and basic moieties which can modify the effective pK values of the single moieties.

Once the suitable supporting solution of the dalbaheptide antibiotic has been prepared, the IEF purification may be accomplished according to methodologies similar to those known in the art.

Accordingly, a set of chambers is prepared, which chambers are determined by a number of isoelectric membranes having increasing pI values. The range of the pI values of the membranes will be set according to the determined pI value of the compound to purify and the pI values of the impurities to separate. Depending on the specific dalbaheptide to purify, the pI value of the membranes can vary from about 3 to about 9. In general, the range of the pI values will be about ±2 the pI value of the compound to purify. A suitable method for preparing the membranes is disclosed in ref. 5 and 113.

The components of the mixture to be purified will thus be separated across the isoelectric gradient, according to their specific pI values; at the end of the process, each chamber will contain the substance (impurity or main compound) having a pI value comprised between the pI values of the two isoelectric membranes delimiting the chamber. For obtaining good purification results the pI value of the compound to be purified should, of course, differ at least to a minimal extent with the pI values of the impurities; however, the pI values delimiting a single chamber may be very close to each other, thus allowing very high levels of purification.

It should be noted, that when the single antibiotic factors of a complex (or at least its main factors) have similar pI values, it is possible to collect all these factors in a single chamber, provided that the undesired impurities have pI values outside the pI range of the antibiotic factors; in this way, the active antibiotic compounds may be separated as a whole from the undesired impurities, without the need of separating each single factor. Thus, in the following of this specification, the wording "main component" refers to a single factor of an antibiotic complex as well as to a mixture of factors having similar pI values.

A suitable apparatus for carry out the present IEF purification is described in ref. 113.

According to the present invention, the compound to be purified may continuously be loaded into the chamber where the main component is isoelectric; in this way, under the electrophoretic titration process conditions, the desired compound(s) remains trapped into that chamber, while impurities having different pI values or being non-isoelectric are forced to leave the chamber, towards the more anodic or cathodic chambers. If desired, each chamber may be connected with a liquid reservoir, in order to provide a suitable recycling of the chamber for avoiding undesired precipitation of the product. This option is particularly suitable when applied to the chamber of the main component; in fact, as the IEF process takes place, the concentration of the product into the chamber (which has a relatively small volume) may increase up to the precipitation value; as said above, this event should be strictly avoided, as with the main component also impurities would co-precipitate. On the other hand, a concentration of the impurities into the other chambers may be desired and thus the above recycling would not be necessary.

In an alternative embodiment of the present purification process, the compound to be purified may be continuously loaded into a chamber where the main component is not isoelectric, so that it is forced to move towards its isoelectric chamber. This alternative process is particularly suitable for separating impurities having a pI very close to the one of the main component. It could in fact happen that, when the mixture to be purified is loaded into its isoelectric chamber, an impurity having a pI value close to the one(s) of the main component would remain into that chamber instead of moving towards the respective neighboring anodic or cathodic chamber, where the impurity is isoelectric. Thus, by loading the compound to be purified into a chamber where the main component is not isoelectric, for instance in the neighboring anodic chamber, the main component moves towards its isoelectric chamber, while the impurities having more anodic pI values are left in the initial chamber.

As above, a liquid reservoir may be connected with each chamber; of course, for avoiding precipitation of the main component, the liquid reservoir should be connected also in this case to the chamber where the main component is isoelectric.

The applied voltage will depend upon a number of factors such as the type of the substance to be purified, the amount of impurities present, the amount of the substance loaded, the composition of the supporting solution as well as the composition of the anolyte and the catholyte, and the geometry of the IEF apparatus (e.g. dimension, number of isoelectric membranes, distance of the electrodes etc.); for instance, a low voltage is in general applied for eliminating excess salt in the sample, before beginning the purification process at a higher voltage; for instance, for a 12 cm distance of the electrodes, an initial voltage from 400 V to 600 V can be applied, and afterword the process is performed at a voltage of from 1000 to 5000 V, preferably about 1500 V.

The heat which forms during the electrophoretic process may be dissipated according to known per se techniques; for reduced heating, dissipation in air at room temperature is sufficient, while for a more intehensive heating a circulating coolant, such as water, may be preferred.

The process time will depend mainly on the amount of substance loaded and on the applied voltage.

After the IEF purification has been carried out, the desired compound is recovered from the supporting solution according to known per se techniques. For instance, the separation of the purified compound from the urea/CHAPS mixture may be carried out on a silanized silica gel column.

The following examples will illustrate more in detail the invention.

This specific examples refer to the purification of the $6^B$-decarboxy-$6^B$-(hydroxymethyl)-$N^{63}$-3-(dimethyl-amino) propyl amide derivative (hereinafter "amide derivative") of antibiotic A40926, obtained according to the amidation process disclosed in ref. 101 by reacting the $6^B$-decarboxy-$6^B$-(hydroxymethyl) antibiotic A40926 with dimethylpropylamine in the presence of the condensing agent PyBOP. During pharmacological studies, it has been found that such amide derivative complex contains undesired impurities which may elicit an histamine release effect. With the process of the present invention, it is possible to remove said undesired impurities, thus obtaining a purified product showing no histamine release effect.

As known, antibiotic A40926 obtained from the fermentation process (see ref. 21) is a mixture of single related factors, wherein the main factors are factor $B_0$ and factor $B_1$. The ratio of the single factors may be varied by modifying the fermentation conditions (see, e.g., ref 115). Furthermore, if desired, the single factors of A40926 may be first separated and then mixtures of the single factors in the desired ratio may be prepared.

As evident, the relative amide derivatives of a A40926 complex will thus be a corresponding mixture of the amide derivatives of the single factors, depending on the composition of the specific antibiotic A40926 starting material.

In the following of this specification, when dealing with mixtures of amide derivatives of factor $B_0$ and $B_1$, it is intended a mixture of the two factors in any proportion.

The above amide derivative of A40926 factor $B_0$ and factor $B_1$ may be represented by the following formula:

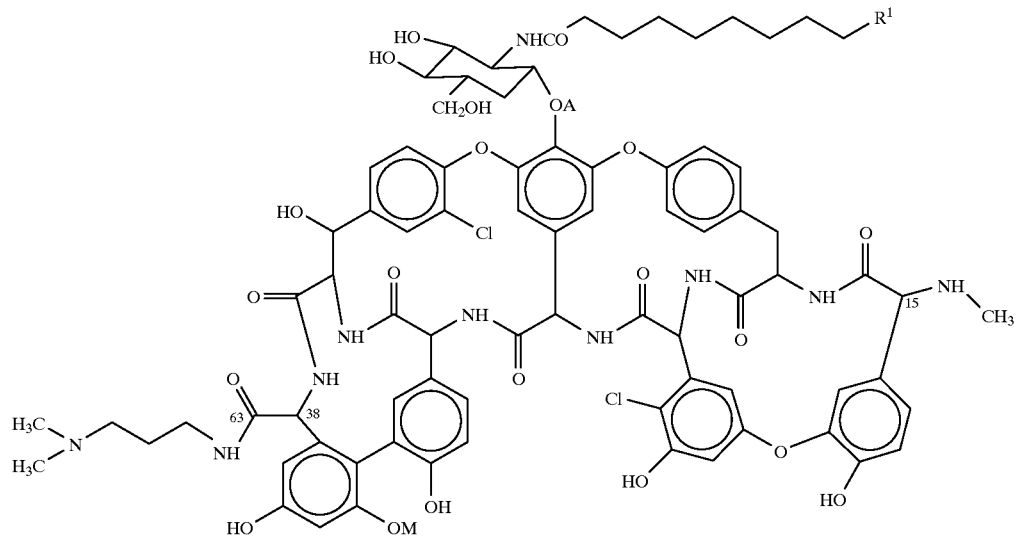

wherein M represents a mannosyl moiety and $R_1$ represents a —$CH(CH_3)_2$ group for factor $B_0$ or a —$(CH_2)_2CH_3$ group for factor $B_1$.

Thus, according to the present invention, the above amide derivatives of A40926 may be obtained substantially free from undesired impurities, as a mixture of amides of factors $B_0$ and $B_1$. It is intended that a substantially pure mixture of amides of factors $B_0$ and $B_1$ is a mixture of the said two compounds in any proportion, which mixture is free from undesired impurities having a pI value within the range from about 8.40 to about 8.65, determined in a solution of 8M urea and 3.5% (w/v) CHAPS. In order to obtain said purified mixture, the two limiting membranes of the collecting chamber may be set at a pI value of 8.41 and 8.65, respectively, while loading the mixture to be purified in this electrolyzer chamber.

If desired, the minor factor $B_1$ may be separated from the main factor $B_0$, thus obtaining the substantially pure amide derivative of factor $B_0$. It is intended that a substantially pure amide derivative of factor $B_0$ is a compound which is free from undesired impurities having a pI value within the range from about 8.45 to about 8.65, determined in a solution of 8M urea and 3.5% (w/v) CHAPS. In order to obtain the above pure compound, the two limiting membranes of the collecting chamber may be set at a pI value of 8.45 and 8.65, respectively; in this case, the mixture to be purified is preferably loaded in the nearest anodic chamber.

ANALYTICAL RP-HPLC SYSTEM

Apparatus: two Mod. 305 pumps, a Mod. 232 autosampler, a Mod. 805 manometer, a Mod. 811B dynamic mixer (all from Gilson Medical Electronic, Middletown, Wis., USA);

column: YMC-Pack C4-AMP 5 μm, 20 nm, 250×4.6 mm (YMC Co. Ltd., Shin-Arami Tai Kumijama-cho, Kusegun, Kyoto, Japan);

Elution:
  phase A: water/acetonitrile/phosphoric acid (95/5/0.05),
  phase B: water/acetonitrile/phosphoric acid (5/95/0.05),
  gradient profile: time(min): 2 25 35 55 60 64 65
    % B: 5 20 20 40 95 95 5
  volume injection: 100 μl,
  flow rate: 1.8 ml/min,
  oven temperature: 30° C.;

detection: UW absorbance at 254 nm on a Mod. 116 UV detector (Gilson Medical Electronic, Middletown, Wis., USA).

EXAMPLE 1

Preparation of Analytical Immobilized pH Gradient (IPG) Gels, for Determining the pI Values of the Main Component and of the Impurities Gel dimension: 25×10 cm, 0, 5 mm thick; pH interval: 7.0 to 10.0.

The IPG ranges are set in a 5% T, 4% C polyacrylamide matrix, according to the preparation recipe disclosed in Ref. 110. After preparing the two limiting, acidic and basic mixtures, they are titrated (with a weak acid and a weak base) to pH values close to neutrality. This is important in order to ensure uniform polymerization and efficient monomer conversion throughout the preformed pH gradient. Upon gel washing in distilled water (3×30 min), all added titrants (as well as catalysts and ungrafted monomers) are efficiently removed. The gels are then equilibrated for 30 min in 2% glycerol solution, dried in air and reswollen in a mixture of 8M urea and 3.5% CHAPS, overnight. The sample is applied in surface wells at the anodic gel side in concentrations from 80 to 600 μg/track. After an initial 1 h period at 500 V, focusing is continued at 2500 V for 6 h at 20° C.

For gel staining a colloidal dispersion of Coomassie Brilliant Blue G.250 in 12.5% TCA, in a leuco form, has been adopted (see ref. 111), overnight. Color enhancement is obtained by rinsing in plain distilled water.

Figure 2:
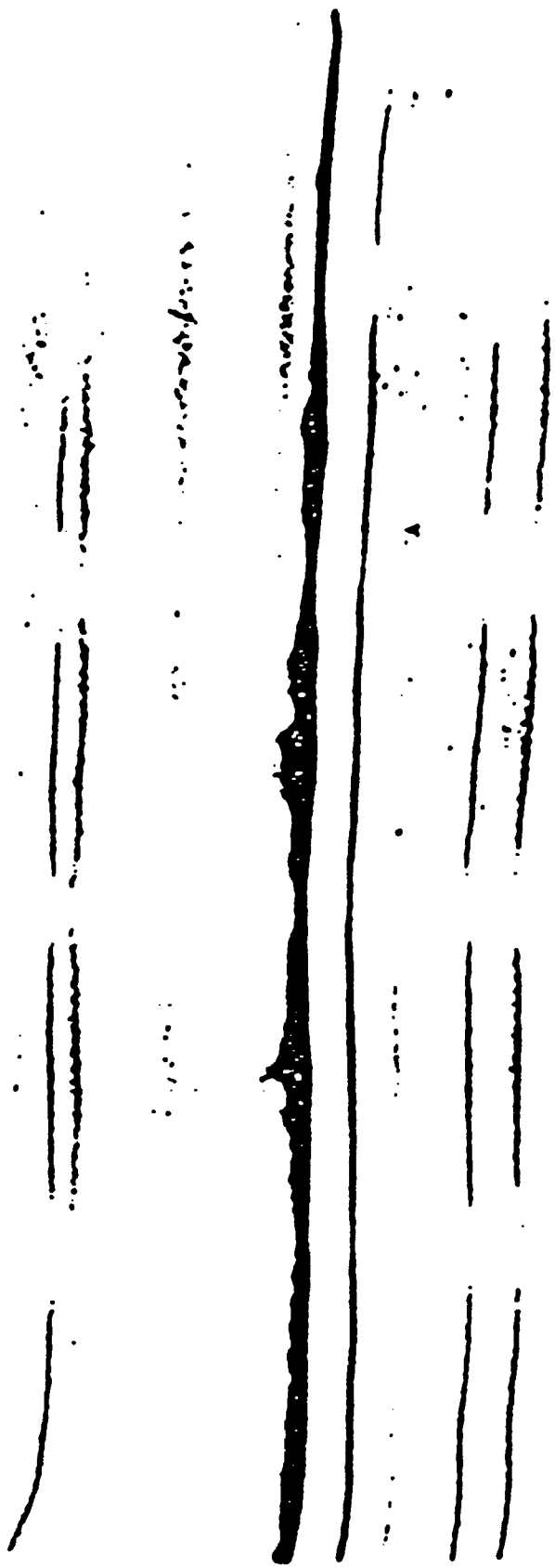
FIG. 2: Analytical IPG of the unfractionated sample, according to Example 1; sample load ranges from 80 (right side) to 600 (left side) μg per track.

FIG. 2: Shows the results of the analytical IPG.

For exactly determining the pI value of the amide derivative of factor $B_0$ and factor $B_1$, the above procedure is repeated under the same conditions, in the pH interval from 8.0 to 9.0 using a mixture of 8M urea and 1% CHAPS. The so determined pI value of the amide derivative of factor $B_0$ is 8.56, whilst the pI value of the amide derivative of factor $B_1$ is 8.40.

EXAMPLE 2

IEF Purification of the Sample (Amides of Antibiotic A40926 Factors $B_0$ and $B_1$)

The IEF purification is carried out with the Iso-PrIME apparatus (Hoefer Sci., San Francisco), consisting of a multichamber electrolyzer to be assembled with isoelectric, buffering membranes.

A) Preparation of Isoelectric Immobilized Membranes

After determining, in the above analytical gels, the precise pI values of the main fraction and of the impurities, six isoelectric membranes are prepared having the following pI values: 7.00, 8.31, 8.41, 8.46, 8.65 and 9.50. All membranes were cast as a 10% T, 4% C matrix in the form of disks of 4.7 cm diameter of and a thickness of ca. 1 mm; the membranes are supported by glass fiber filters (see ref. 5 and 113 for a detailed description of their properties and preparation).

B) Experimental Conditions

Anolyte: 5 mM acetic acid in 8 M urea and 0.1% CHAPS (pH 4.84, conductivity; 85.5 μmhos);

Supporting solution in the chambers: mixture of 8 M urea and 3.5% CHAPS;

Supporting solution in the electrodic reservoires: 8 M urea and 0.1% CHAPS:

After an initial low-voltage run (500 V) for eliminating excess salt in the sample, purification is achieved at 1500 V (over a 12 cm electrode distance) in 30 hours. No circulating coolant is utilized and joule heat was dissipated in air at room temperature (22° C.). Under the above conditions, the temperature rise in the liquid in the electrolyzer, at steady-state, was only 3° C.

C) Purification Process

A preparative run is carried out, by loading 500 mg of sample (dissolved in 100 ml of 8 M urea and 3.5% CHAPS) in chamber 3 of the multicompartment electrolyzer (in between the pI 8.41 and pI 8.65 membranes, where the main component would be trapped isoelectrically). The content of this chamber is recycled from a reservoir, whereas all neighboring chambers were not connected to any reservoir. Since the liquid content of each chamber of the electrolyzer is 5 ml, whereas in chamber 3 (chamber plus reservoir) it is 100 ml, this results in collection, in neighboring chambers, of 20-fold concentrated impurities.

The preparative run results are summarized in FIGS. 3 to 6, where the RP-HPLC analysis of each chamber is shown.

Figure 1:
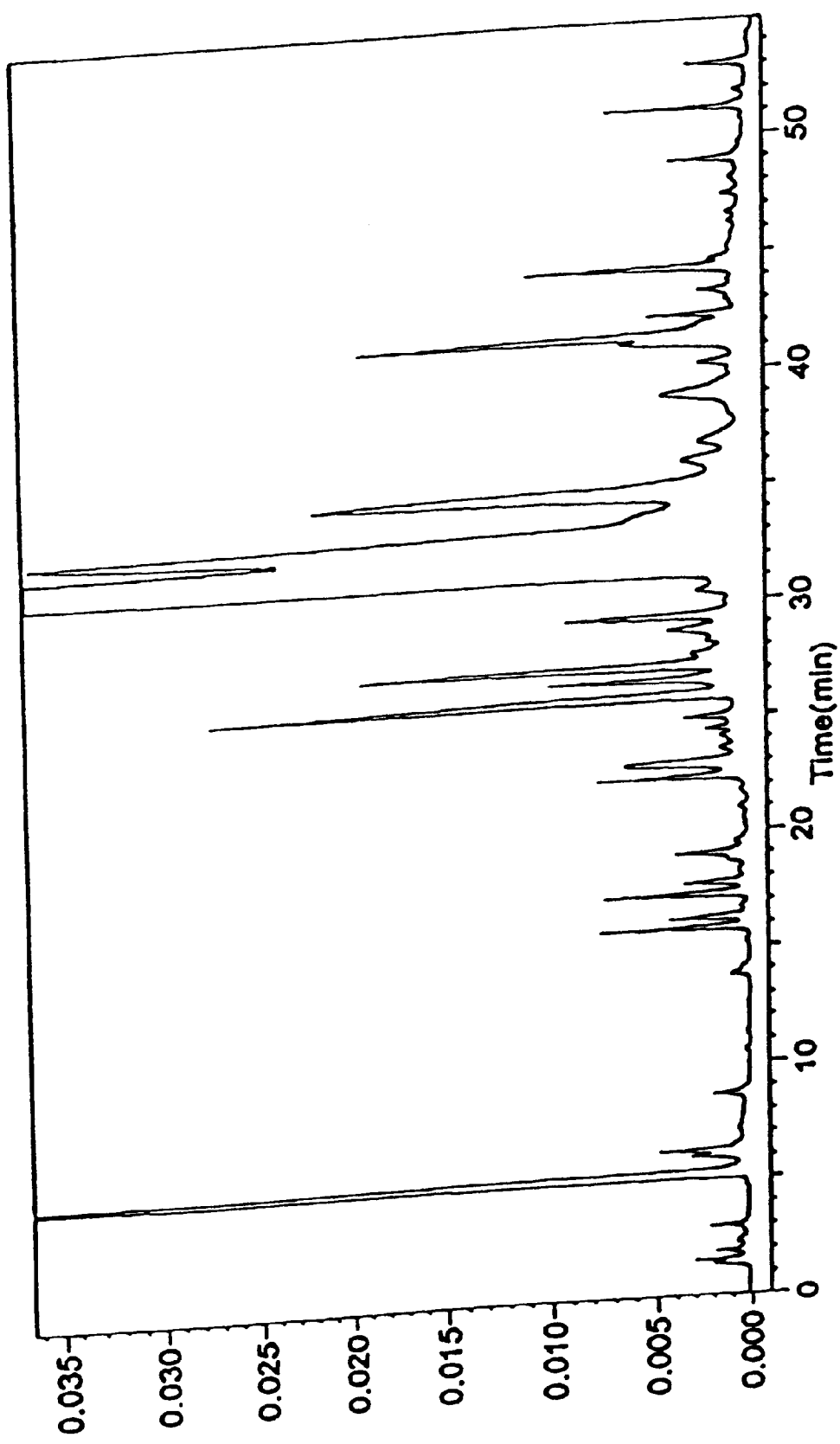
FIG. 1: Analytical RP-HPLC of the unfractionated sample; the main peak relates to the amide derivatives of factors $B_0$ and $B_1$.

FIG. 1 gives the total spectrum of components, as seen by under heavy overloading of the main components. While it is not possible to fully compare the elution order in RP-HPLC with the pI spectrum, component $B_1$ is clearly identifiable with the compound having the nearest anodic pI value with respect to component $B_0$.

Figure 4:
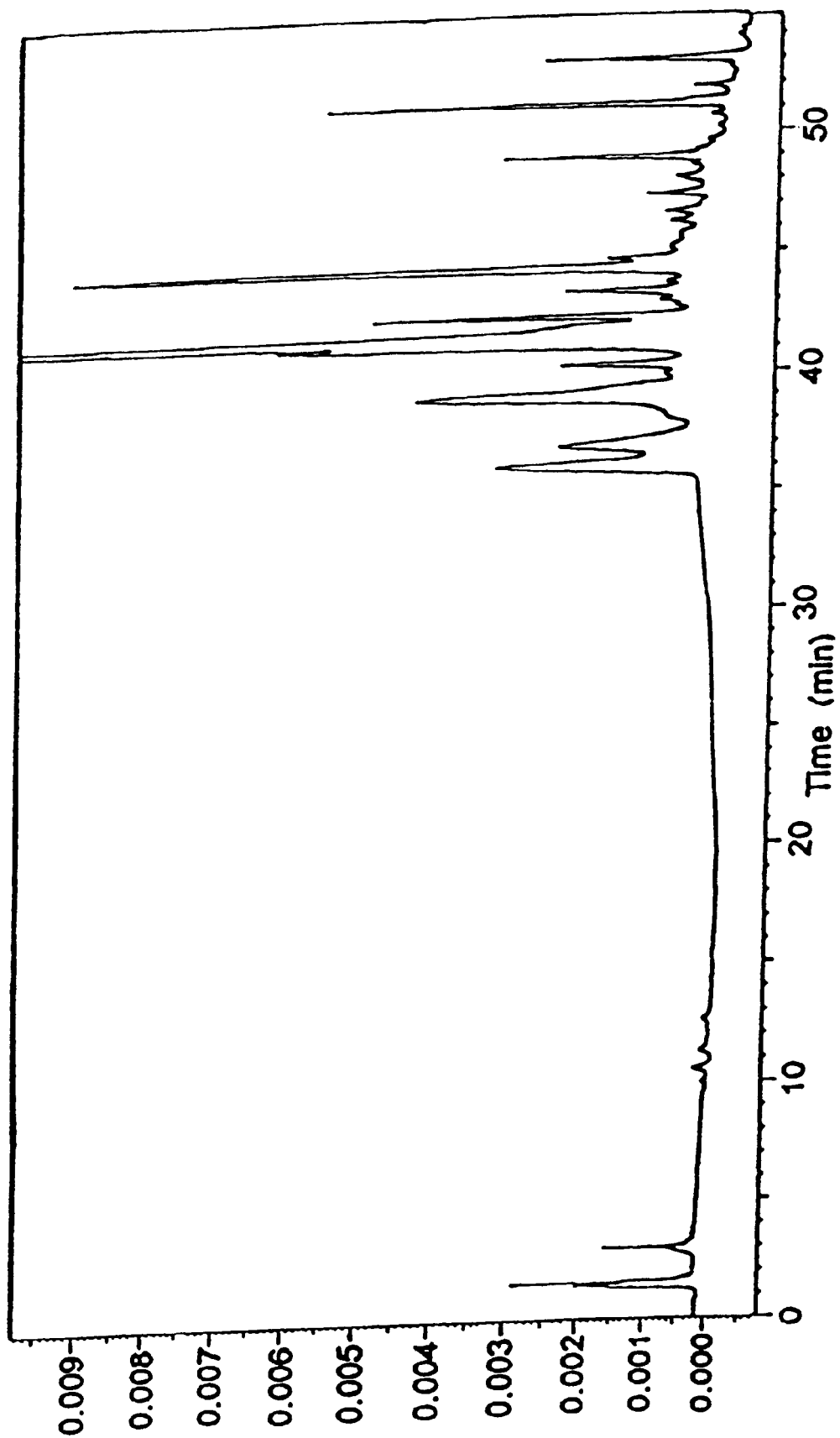
FIGS. 4–6: Analytical RP-HPLC of the content of chambers 1, 2 an 4 (chambers where impurities are collected) after the IEF purification process according to Example 2.
Figure 5:
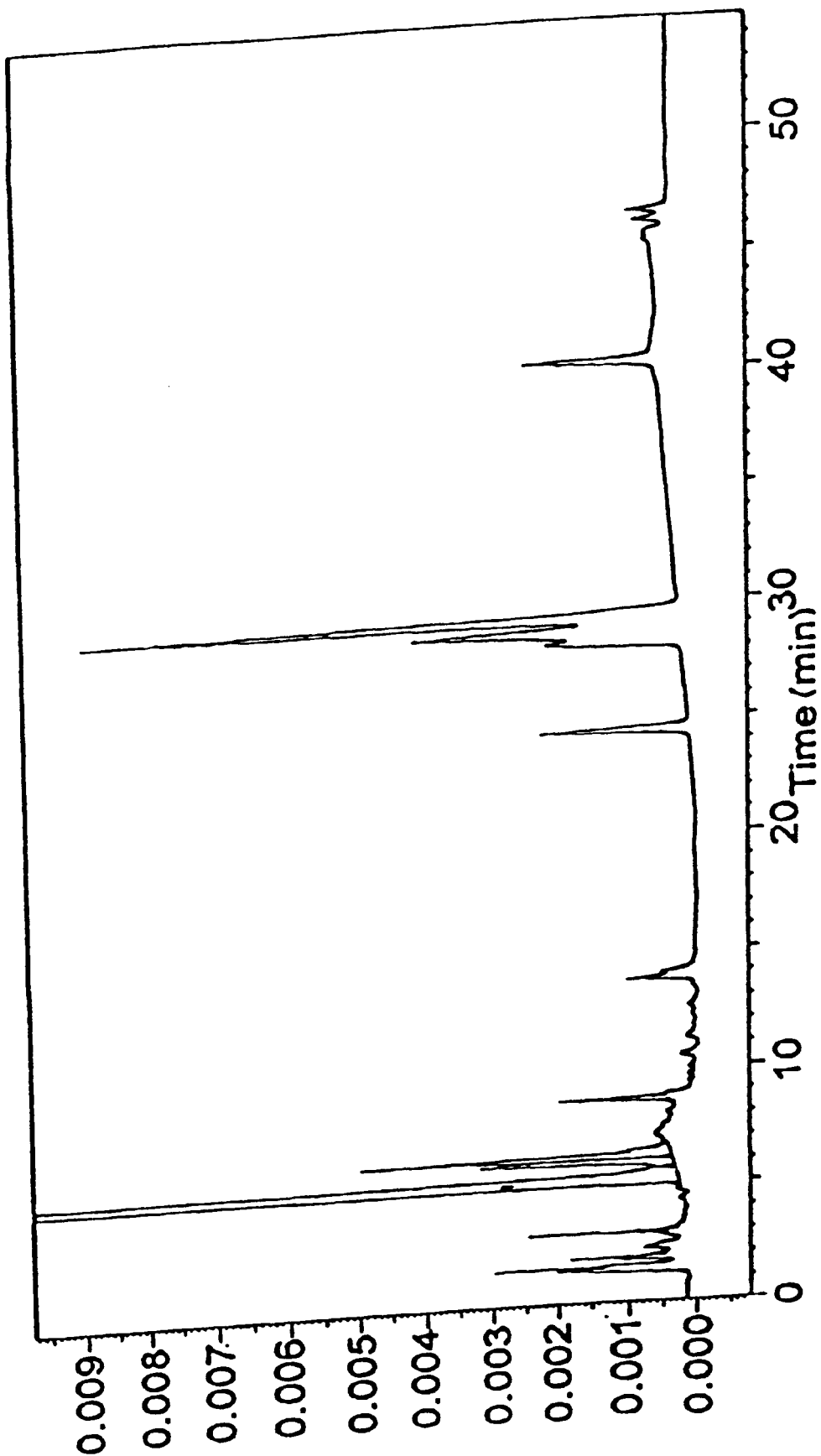
Figure 6:
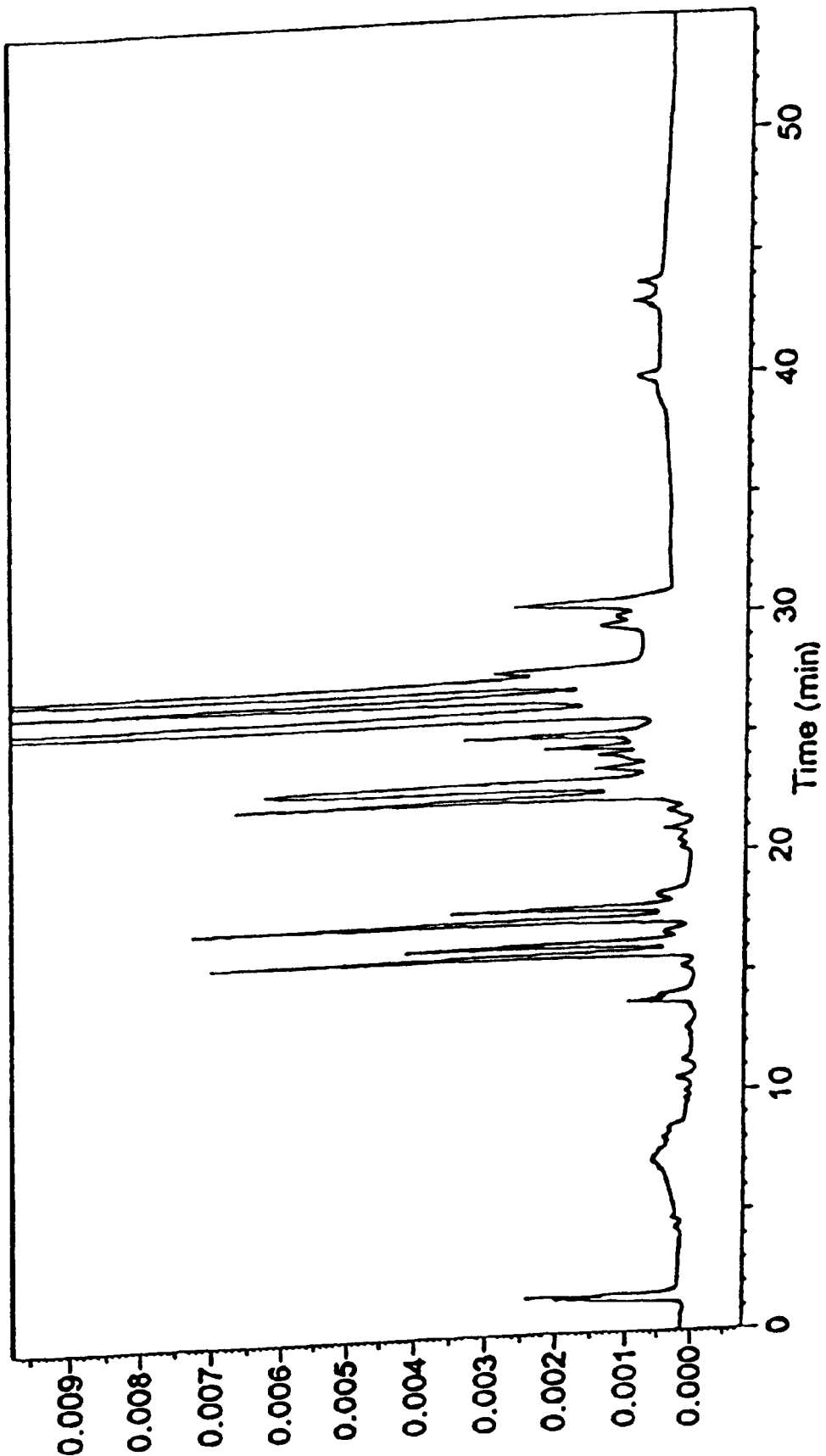

The spectrum of components collecting in chamber 1 of the electrolyzer (in between the pI 7.0 and pI 8.31 membranes) is shown in FIG. 4; those impurities concentrated in chamber 2 (pI 8.31 to pI 8.41 membranes) are shown in FIG. 5; those impurities concentrated in the last chamber (No. 4, in between the pI 8.65 and pI 9.5 membranes) are shown in FIG. 6.

Figure 3:
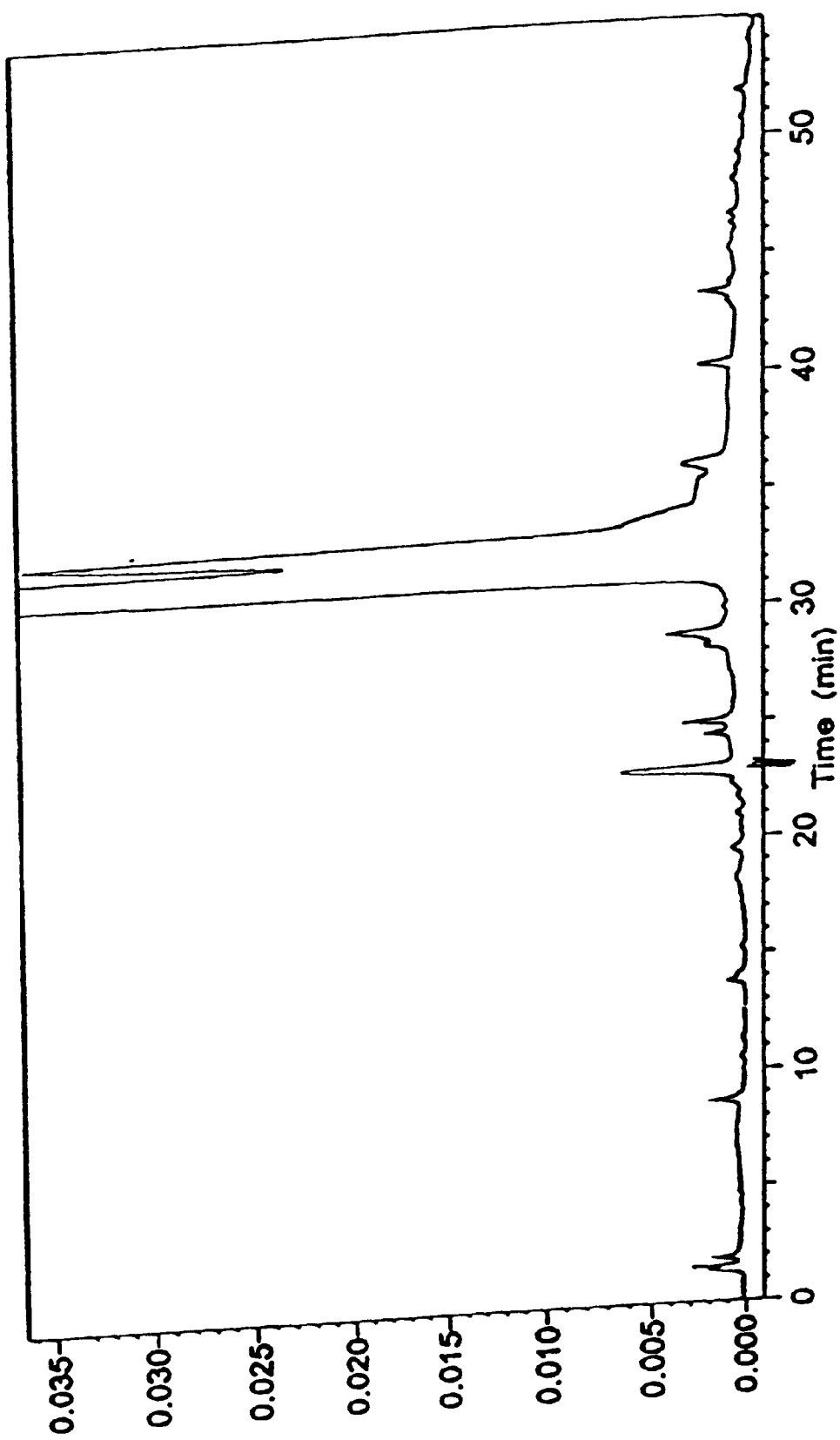
FIG. 3: Analytical RP-HPLC of the content of chamber 3 (pI 8.41÷8.65, chamber where the main purified fraction is collected) after the IEF purification process according to Example 2. The main peak corresponds to the amide derivative of factor $B_0$; the smaler peak overlapping this peak corresponds to the amide derivatives of factor $B_1$.

The main component (collecting in chamber 3, in between the pI 8.41 and pI 8.65 membranes) is shown in FIG. 3; the smaller peak close to the main peak corresponds to the amide derivatives of factor $B_1$.

EXAMPLE 3

Pure Amide Derivatives of A40926 Factor $B_0$

Example 2 is repeated under the same experimental conditions, with the only difference that the pI range of chamber 3 is now 8.46÷8.65 and that the sample (500 mg) is loaded into the nearest anodic chamber (chamber 2) instead of into chamber 3; the content of chamber 3 (where the main component is forced to move and is trapped isoelectrically) is recycled from a reservoir.

Figure 7:
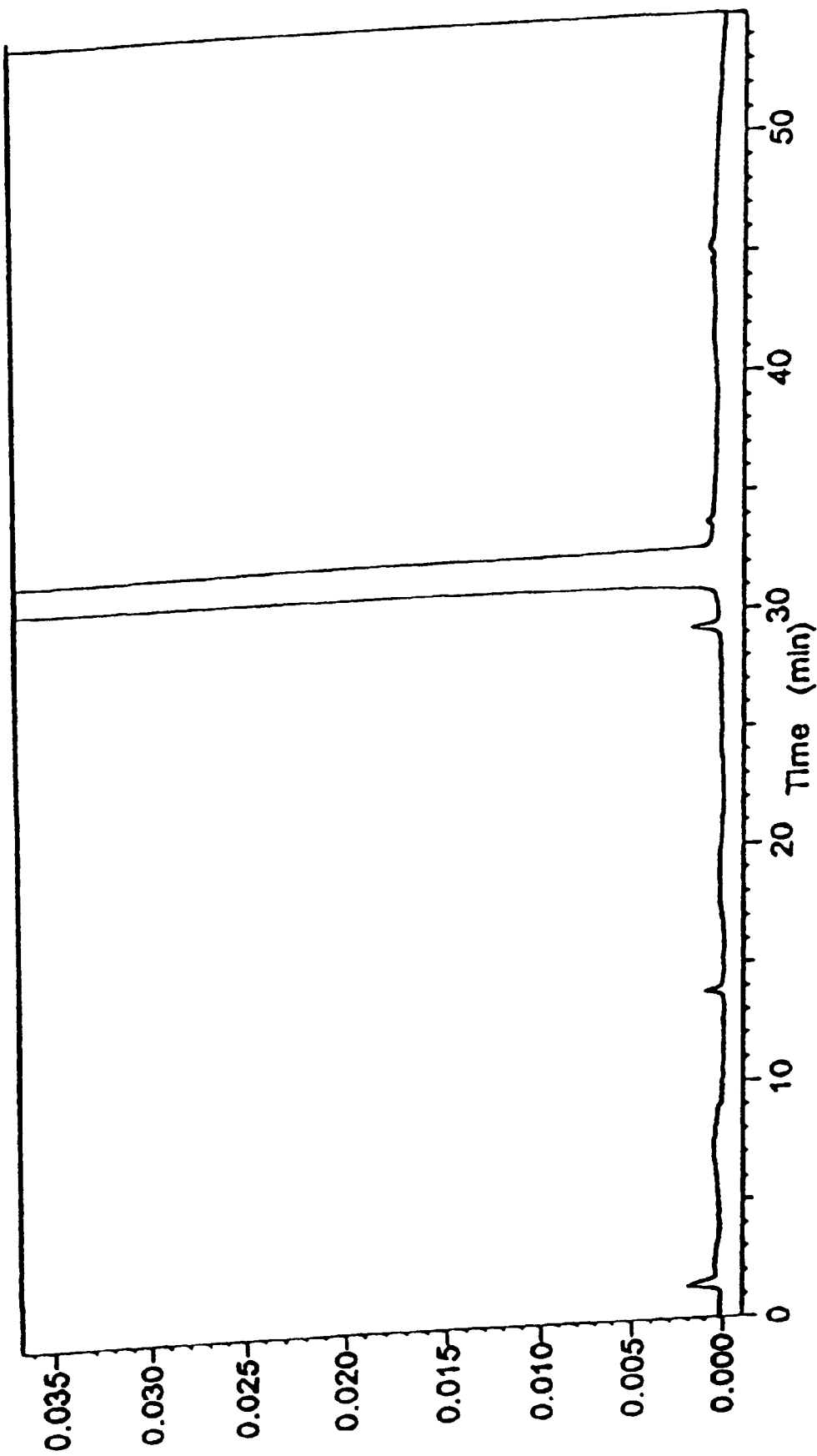
FIG. 7: Analytical RP-HPLC of the content of chamber 3 (pI 8.46÷8.65, chamber where the purified amide derivative of factor $B_0$ is collected) after the IEF purification process according to Example 3. The main peak corresponds to the pure amide derivative of factor $B_0$.

FIG. 7 shows the results of this purification; the smaller peak close to the main peak of the amide derivative of A40926 factor $B_0$ is absent, thus indicating the absence of the $B_1$ amide derivatives of A40926.

EXAMPLE 4

Separation of the Amide Derivative of A40926 Factor $B_0$ from the Urea/CHAPS Supporting Mixture The final solution contained in chamber 3 (200 mg in 50 ml), obtained according to example 3, is diluted with 0.5M TRIS (450 ml, pH 9) and applied on the top of silanized silica gel column (16×250 mm), using a Miniplus 3 peristaltic pump (Gilson) at a flow rate of 4 ml/min; methanol is employed as the eluent.

Before applying the solution the column is washed with TRIS buffer (0.5M, pH 9).

After applying the solution, the column is first washed with TRIS buffer (0.5M, pH 9) down to the zero of optical density and then with distilled water for removing the salts.

The monitoring of the eluates solution is carried out with a UV detector mod. 2138 unicords (LKB, Uppsala. Sweden) at 280 nm.

Fractions showing optical density different from zero were collected and analyzed by RP-HPLC (see the above methodology) and TLC on silica gel F254 (Merck, Darmstadt, Germany), mobile phase $CHCl_3/CH_3OH/NH_4OH$ (50/47/3) or $CH_3CN/H_2O/CH_3COOH/CH_3OH$ (50/20/15/5), visualization with UV lamp or iodine vapors.

Fractions containing the pure amide derivatives of A40926 factor $B_0$ are pooled, concentrated under vacuum and lyophilized.

REFERENCE

No.
1. F. Parenti and B. Cavalleri, "Novel glycopeptide antibiotics of the dalbaheptide group", Drugs of the future, Vol. 15 (1), pp. 57–72, (1990).
2. B. Cavalleri and F. Parenti, "Glycopeptides (dalbaheptides)", Kirk-Othmer's Encyclopedia of Chemical Technology, Vol. 2, pp. 995–1018, J. Wiley & Sons, 1992.
3. Sztaricskai, F., and Bognar, R. The Chemistry of the Vancomycin Group of Antibiotics. In: Recent Developments in the Chemistry of Natural Carbon Compounds. Vol.X. R. Bognar and Cs. Szantay (Eds.). Akademiai Kiado 1984; 91–201.

4 European Patent Appl. Publ. No. 448 940
5 Righetti P. G., Wenisch E. and Faupel M. (1989) J. Chromatogr. 475, 293–309
6 Williams, D. H., Rajananda, V., Bojesen, G. and Williamson, M. P. Structure of the antibiotic ristocetin A . J.C.S. Chem. Comm. 1979: 906–908
7 Debono, M., Merkel, K. E., Molloy, R. M., Barnhart, M., Presti, E., Hunt, A. H. and Hamill, R. L. Actaplanin, new glycopeptide antibiotics produced by Actinoplanes missouriensis. The isolation and preliminary chemical characterization of actaplanin, J Antibiot 1984; 37:85–95
8 Hunt, A. H., Elzey, T. K., Merkel, K. E. and Debono, M. Structures of the actaplanins. J Org Chem 1984; 49:641–645
9 Borghi, A., Coronelli, C., Faniuolo, L., Allievi, G., Pallanza, R. and Gallo, G. G. Teichomycins, new antibiotics from Actinoplanes teichomyceticus nov. sp. IV. Separation and characterization of the components of teichomycin (teicoplanin). J Antibiot 1984; 37:615–626
10 Coronelli, C., Gallo, G. G. and Cavalleri, B. Teicoplanin: chemical, physico-chemical and biological aspects. Farm Ed Sci 1987; 42:767–786
11 Barna, J. C. J., Williams, D. H., Stone, D. J. M., Leung, T. W. C. and Doddrell, D. M. Structure elucidation of the teicoplanin antibiotics. J Am Chem Soc 1984; 106:4895–4902
12 Michel, K. H., Shah, R. M. and Hamill, R. L. A35512, a complex of new antibacterial antibiotics produced by Streptomyces candidus. I. Isolation and characterization. J Antibiot 1980; 33:1397–1406
13 Harris, C. M. and Harris, T. M. Structural studies of glycopeptide antibiotic A35512B. Identification of the diphenyl ether-type bis (amino acid). Tetrahedron 1983; 39:1661–1666
14 Eggert, J. H., Michel K. H., Boeck, L. D., Nakatsukasa, W. M. and Kastner, R. E. A41030, a complex of novel glycopeptide antibiotics. Discovery, fermentation, isolation and characterization. 23rd Intersci Conf Antimicrob Agents Chemother (Oct. 24–26, Las Vegas) 1983; Abst 440
15 Hunt, A. H. Dorman, D. E., Debono, M. and Molloy, R. M. Structure of Antibiotic A41030A. J Org Chem 1985; 50:2031–2035
16 Boeck, L. D., Mertz, F. P. A47934, a novel glycopeptide-aglycone antibiotic produced by a strain of Streptomyces toyocaensis. Taxonomy and fermentation studies. J Antibiot 1986; 39:1533–1540
17 Hunt, A. H., Occolowitz, J. L., Debono, M., Molloy, R. M. and Maciak, G. M. A47934 and A41030 factors-new glycopeptides and glycopeptide aglycones: structure determination. 23rd Intersci Conf Antimicrob Agents Chemother (Oct. 24–26, Las Vegas) 1983; Abst 441
18 Sitrin, R. D., Chan, G. W., Dingerdissen, J. J., Holl, W., Hoover, J. R. E., Valenta, J. R., Webb, L. and Snader, K. M. Aridicins, novel glycopeptide antibiotics. II. Isolation and characterization, J Antibiot 1985; 38:561–571
19 Jeffs, P. W., Mueller, L., DeBrosse, C., Heald, S. L. and Fisher, R. Structure of aridicin A. An integrated approach employing 2D NMR, energy minimization, and distance constraints. J Am Chem Soc 1986; 108:3063–3075
20 Roberts, G. D., Carr, S. A., Rottschaefer, S. and Jeffs, P. W. Structural characterization of glycopeptide antibiotics related to vancomycin by Fast Atom Bombardment Mass Spectrometry. J Antibiot 1985; 38:713–720
21 U.S. Pat. No. 4,935,238
22 Riva, E., Zanol, M., Selva, E. and Borghi, A. Column purification and HPLC determination of teicoplanin and A40926. Chromatographia 1987; 24:295–301.
23 Waltho, J. P., Williams, D. H., Selva, E. and Ferrari, P. Structure elucidation of the glycopeptide antibiotic complex A40926. J Chem Soc, Perkin Trans I, 1987; 2103–2107
24 Folena-Wasserman, G., Poehland, L. B., Yeung, E. W-K., Staiger, D., Kilimer, L. B., Snader, K., Dingerdissen, J. J. and Jeffs, P. W. Kibdelins (AAD-609), novel glycopeptide antibiotics. II. Isolation, purification, and structure. J Antibiot 1986; 39:1395–1406
25 Christensen, S. B., Allaudeen, H. S., Burke, M. R., Carr, S. A., Chung, S. K., DePhillips, P., Dingerdissen, J. J., DiPaolo, M., Giovenella, A. J., Heald, S. L., Killmer, L. B., Mico, B. A., Mueller, L., Pan, C. H., Poehland, B. L., Rake, J. B., Roberts, G. D., Shearer, M. C., Sitrin, R. D., Nisbet, L. J. and Jeffs, P. W. Parvodicin, a novel glycopeptide from a new species, Actinomadura parvosata: discovery, taxonomy, activity and structure elucidation, J Antibiot 1987; 40:970–990
26 U.S. Pat. No. 4,954,482
27 U.S. Pat. No. 4,521,335
28 U.S. Pat. No. 4,882,313
29 European Patent Appl. Publ. No. 255 256 (Claiming priority of U.S. patent application Ser. No. 892027 filed on Jul. 30, 1986)
30 U.S. Pat. No. 4,322,343
31 U.S. Pat. No. 4,563,442
32 U.S. Pat. No. 4,504,467
33 U.S. Pat. No. 4,497,802
34 Huber, F. M., Michel, K. H., Hunt, A. J., Martin, J. W., and Molloy, R. M. Preparation and characterization of some bromine analogs of the glycopeptide antibiotic actaplanin. J. Antibiot. 1988; 41:798–801
35 U.S. Pat. No. 2,951,766
36 Cometti, A., Gallo, G. G., Ketternring, J., Pallanza, R., Panzone, G. B., Tuan, G., and Zerilli, L. F. Isolation and structure determination of the main related substances of teicoplanin, a glycopeptide antibiotic. II Farmaco, Ed. Sci., 1988; 43:1005–1018
37 Borghi, A., Antonini, P., Zanol, M., Ferrari, P., Zerilli, L. F., and Lancini, G. C. Isolation and structure determination of two new analogs of teicoplanin, a glycopeptide antibiotic. J. Antibiotic 1989; 42:361–366
38 Malabarba, A., Ferrari, P., Gallo, G. G., Kettenring, J. and Cavalle ri B. Teicoplanin, antibiotics from Actinoplanes teichomyceticus nov. sp. VII. Preparation and NMR characteristic of the aglycone of teicoplanin. J Antibiot 1986; 39:1430–1442
39 Malabarba, A., Strazzolini, P., DePaoli, A., Landi, M., Berti, M. and Cavalleri, B. Teicoplanin, antibiotics from Actinoplanes teichomyceticus nov. sp. VI. Chemical degradation: physico-chemical and biological properties of acid hydrolysis products. J Antibiot 1984; 37:988–999
40 U.S. Pat. No. 5,064,811
41 U.S. Pat. No. 4,954,483
42 European Patent Appl. Publ. No. 326 873
43 European Patent No. 290 922
44 U.S. Pat. No. 5,194,424
45 European Patent Appl. Publ. No. 316 712
46 U.S. Pat. No. 5,185,320
47 U.S. Pat. No. 4,782,042
48 U.S. Pat. No. 4,868,171
49 Int. Pat. Appl. Publ. No. WO 88/02755 (design. US)
50 U.S. Pat. No. 4,804,534
51 Kamogashira, T., Nishida, T. and Sugawara, M. A new glycopeptide antibiotic, OA-7653, produced by Streptomyces hygroscopicus subsp. hiwasaensis. Agric Biol Chem 1983; 47:499–506

52 Jeffs, P. W., Yellin, B., Mueller, L. and Heald, S. L. Structure of the antibiotic OA-7653. J Org Chem 1988; 53:471–477

53 Boeck, L. D., Mertz, F. P., Wolter, R. K. and Higgens, C. E. N-Demethyl vancomycin, a novel antibiotic produced by a strain of *Nocardia orientalis*. Taxonomy and fermentation. J Antibiot 1984; 37:446–453

54 Hunt, A. H., Marconi, G. G., Elzey, T. K. and Hoehn, M. M. A51568A: N-Demethylvancomycin. J Antibiot 1984; 37:917–919

55 European Patent Appl. Publ. No. 159 180

56 European Patent Appl. Publ. No. 231 111

57 Tsuji, N., Kobayashi, M., Kamigauchi, T., Yoshimura, Y. and Terui, Y. New glycopeptide antibiotics. I. The structures of orienticins. J Antibiot 1988; 41:819–822

58 Gauze, G. F., Brazhnikova, M. G., Laiko, A. V., Sveshnikova, M. A., Preobrazhenskaya, T. P., Fedorova, G. B., Borisova, V. N., Tolslykh, I. V., Yurina, M. S., Pokras, L. S., Goldberg, L. E., Malkova, I. V. and Stepanova, E. S. Eremomycin, a novel cyclic glycopeptide antibiotic. Antibiot Med Biotecknol 1987; 32:571–576

59 Brazhnikova, M. G. Properties of eremomycin, a new glycopeptide antibiotic. 2nd Int Symp on "New Bioactive Metaboliles from Microorganisms" (May 2–7, Gera) 1988; Post 40

60 Berdnikova, T. F., Tokareva, N. L., Abramova, E. A., Dokshina, N. Y., Potapova, N. P. and Lomakina, N. N. Structure of the aglycone of eremomycin, a novel antibiotic of the group of polycyclic glycopeptides. Antibiot Kimioter 1988; 33:566–70

61 Lomakina, N. N., Tokareva, N. L. and Potapova, N. P. Structure of eremosamine, an amino sugar from eremomycin. Antibiot Kimioter 1988; 33:726–729

62 Riva, E., Gastaldo, L., Beretta, M. G., Ferrari, P., Zerilli, L. F., Cassani, G., Goldstein, B. P., Berti, M., Parenti, F. and Denaro, M. A42867, a novel glycopeptide antibiotic. J Antibiot. 1989; 42:497–505

63 Hamill, R. L., Baker, P. J., Berry, D. M., Debono, M., Molloy, R. M. and Moreland, D. S. A82846, a new glycopeptide complex, produced by *Amycolatopsis orientalis*. 2.Isolation and characterization. 28th Intersci Conf Antimicrob Agents Chemother (Oct. 23–26, Los Angeles) 1988; Abst 975

64 Hunt, A. H., Occolowitz, J. L., Debono, M., Molloy, R. M. A82846, a new glycopeptide complex, produced by *Amycolatopsis orientalis*. 3. Structure determination. 28th Intersci Conf Antimicrob Agents Chemother (Oct. 23–26, Los Angeles) 1988; Abst 976

65 Tsuji, N., Kamigauchi, T., Kobayashi, M. and Terui, Y. New glyco peptide antibiotics: II. The isolation and structures of chloro orienticins. J Antibiot 1988; 41:1506–1510

66 European Patent Appl. Publ. No. 273 727 (Claiming priority of U.S. patent application Ser. No. 948175 filed on Dec. 30, 1986)

67 U.S. Pat. No. 4,552,701

68 European Patent Appl. Publ. No. 201 251 (claiming priority of U.S. patent application Ser. No. 726731 filed on Apr. 25, 1985 and U.S. patent application Ser. No. 853583 filed on Apr. 18, 1986)

69 U.S. Pat. No. 4,698,327

70 U.S. Pat. No. 4,639,433

71 U.S. Pat. No. 4,643,987

72 Harris C. M., Kannan R., Kopecka H., and Harris T. M. The role of the chlorine substituents in the antibiotic vancomycin:preparation and characterization of mono- and didechlorovancomycin. J. Am. Chem. Soc. 1985; 107:6652–6658

73 European Patent No. 218 099

74 U.S. Pat. No. 5,198,418

75 Batta, G., Sztaricskai, F., Csanadi, J., Kamaromi, I. and Bognar, R. 13C NMR study of actinoidins: carbohydrate moieties and their glycosidic linkages. J Antibiot 1986; 39:910–913

76 Heald, S. L., Mueller, L. and Jeffs, P. W. Actinoidins A and A2: structure determination using 2D NMR methods. J Antibiot 1987; 40:630–645

76 Heald, S. L., Mueller, L. and Jeffs, P. W. Actinoidins A and A2: structure determination using 2D NMR methods. J Antibiot 1987; 40:630–645

77 Okazaki, T., Enokita, R., Miyaoka, H., Takatsu, T. and Torkiata, A. Chloropolysporins A, B and C, novel glycopeptide antibiotics from *Faenia interjecta* sp.nov. I. Taxonomy of producing organism. J Antibiot 1987; 40:917–923

78 Takatsu, T., Nakajima, M., Oyajima, S., Itoh, Y., Sakaida, Y., Takahashi, S. and Haneishi, T. Chloropolysporins A, B and C, novel glycopeptide antibiotics from *Faenia interjecta* sp. nov. II. Fermentation, isolation and physicochemical characterization, J Antibiot 1987; 40:924–932

79 Takatsu, T., Takahashi, S., Nakajima, M., Haneishi, T., Nakamura, T., Kuwano, H. and Kinoshita, T. Chloropolysporins A, B and C, novel glycopeptide antibiotics from *Faenia interjecta* sp. nov. III. Structure elucidation of chloropolysporins. J Antibiot 1987; 40:933–940

80 Dingerdissen, J. J., Sitrin, R. D., DePhillips, P. A., Giovenella, A. J., Grappel, S. F., Mehta, R. J., Oh, Y. K., Pan, C. H., Roberts, G. D., Shearer, M. C. and Nisbet, L. J. Actinoidin A2 a novel glyco peptide: production, preparative HPLC separation and characterization. J Antibiot 1987; 40:165–172

81 Japanese Pat. Appln. Publ. No. 63017897 (Farmdoc Abstract 88-061310)

82 Int. Pat. Appl. Publ. No. WO 90/11300 (design. US)

83 European Patent No. 370 283

84 McGahren, W. J., Leese, R. A., Barbatschi, F., Morton, G. O., Kuck, N. A. and Ellestad, G. A. Components and degradation compounds of the avoparcin complex. J Antibiot 1983; 36:1671–1682

85 European Patent Appl. Publ. No. 276 740

86 U.S. Pat. No. 4,742,045

87 Arjuna Rao, V., Ravishankar, D., Sadhukhan, A. K., Ahmed, S. M., Goel, A. K., Prabhu, N. S., Verma, A. K., Venkateswarlu, A., Allaudeen, H. S., Hedde, R. H. and Nisbet, L. J. Synmonicins: a novel antibiotic complex produced by *Synnemomyces mamnoorii* gen. et. sp. nov. I. Taxonomy of the producing organism, termentation and biological properties, 26th Intersci Conf Antimicrob Agents Chemother (Sep. 28–Oct 1, New Orleans) 1986; Abst 939

88 Verma, A. K., Prakash, R., Carr, S. A., Roberts, G. D. and Sitrin, R. D. Synmonicins: a novel antibiotic complex. II. Isolation and preliminary characterization. 26rd lntersci Conf Antimicrob Agents Chemother (Sep. 28–Oct. 1, Las Vegas) 1986; Abst 940

89 European Patent Appl. Publ. No. 351 597

90 European Patent Appl. Publ. No. 351 684

91 European Patent Appl. Publ. No. 351 685

92 European Pat. Appl. Publ. No. 339 982

93 European Pat. Appl. Publ. No. 365 319

94 Int. Pat. Appl. Publ. WO 89/07612 (design. US)

95 European Pat. Appl. Publ. No. 356 894

96 Int. Pat. Appl. Publ. WO 89/02441 (design. US)

97 European Pat. Appl. Publ. No. 448 940
98 European Patent Appl. Publ. No. 352 538
99 European Patent Appl. Publ. No. 560 795
100 European Patent Appl. Publ. No. 578 644
101 European Patent Appl. Publ. No. 596 929
102 Rilbe, H., (1973) Ann. N.Y. Acad. Sci. 209, 11–22
103 Righetti P. G., Wenisch E., Jungbauer A., Katinger H. and Faupel M. (1990) J. Chromatogr. 500, 681–696
104 Ettori C., Righetti P. G., Chiesa C., Frigerio F., Galli G. and Grandi G. (1992) J. Biotechnol. 25, 307–318
105 Wenisch E., Righetti P. G., and Weber W. (1992) Electrophoresis 13, 668–673
106 Weber W., Wenisch E., Gunther N., Marnitz U., Betzels C. and Righetti P. G. (1994) J. Chromatogr. A 679, 181–189
107 Wenisch E., Vorauer K., Jungbauer A., Katinger H. and Righetti P. G. (1994) Electrophoresis 15, 647–653
108 Breton J., Avanzi N., Valsasina B., Sgarella L., La Fiura A. Breme U., Orsini G., Wenisch E. and Righetti P. G. (1995) J. Chromatogr. A, in press
109 Wenisch E., Schneider P., Hansen S. A., Rezzonico R., and Righetti P. G. (1993) J. Biochem. Biophys. Methods 27, 199–213
110 Righetti P. G. (1990) Immobilized pH Gradients; Theory and Metodology, pp. 64–68, Elsevier, Amsterdam
111 Righetti P. G. and Chillemi F. (1978) J. Chromatogr. 157, 243–251
112 Henner J., Sitrin R. D., (1984) J. Antib., 11, 1475–1478
113 U.S. Pat. No. 4,971,670
114 Sahai et al., Antimicrob. Agents Chemoter. (1990), 34(5), 765–9
115 European Patent No. 259781

We claim:

1. Process for purifying an antibiotic compound of the dalbaheptide family, by means of isoelectric focusing in multicompartment electrolyzer with IMMOBILINE zwitterionic membranes, characterized in that the supporting solution is an aqueous mixture of urea and a detergent which is a sulfobetaine zwitterionic derivative of cholic acid.

2. Process according to claim 1 wherein the detergent is {3-[3-(cholamidopropyl)dimethylammonio]}-1-propanesulfonate.

3. Process according to claim 1, wherein the concentration of urea is from 4M to 8M.

4. Process according to claim 1, wherein the concentration of urea is 8M.

5. Process according to claim 1, wherein the concentration of the detergent is from 1% to 5% (w/v).

6. Process according to claim 1, wherein the concentration of the detergent is from 2% to 4.5% (w/v).

7. Process according to claim 1, wherein the concentration of the detergent is 3.5% (w/v).

8. Process according to claim 1, wherein the dalbaheptide antibiotic belongs to the ristocetin sub-group.

9. Process according to claim 1, wherein the dalbaheptide antibiotic to be purified is ristocetin, actaplanin, teicoplanin, antibiotic A35512, antibiotic A41030, antibiotic A47934, ardacin A, B, C, antibiotic A40926, kibdelin, parvodicin, antibiotic UK 68597, or a natural or semisynthetic derivative of said antibiotics.

10. Process according to claim 1, wherein the dalbaheptide antibiotic to be purified is antibiotic A40926 complex or a natural or semisynthetic derivative thereof.

11. Process according to claim 1, wherein the dalbaheptide antibiotic to be purified is the $6^B$-decarboxy-$6^B$-(hydroxymethyl)-$N^{63}$-3-(dimethylamino)propyl amide derivative of antibiotic A40926 complex.

12. Process according to claim 11, wherein the two limiting membranes of the chamber where the purified product is collected are set at a pI value of 8.41 and 8.65, respectively.

13. Process according to claim 11, wherein the two limiting membranes of the chamber where the purified product is collected are set at a pI value of 8.45 and 8.65, respectively.

* * * * *